(12) United States Patent
Wang et al.

(10) Patent No.: US 12,704,458 B2
(45) Date of Patent: Aug. 11, 2026

(54) CRITICAL ANGLE REFLECTION IMAGING FOR QUANTIFICATION OF MOLECULAR INTERACTIONS

(71) Applicant: ARIZONA BOARD OF REGENTS ON BEHALF OF ARIZONA STATE UNIVERSITY, Scottsdale, AZ (US)

(72) Inventors: Shaopeng Wang, Chandler, AZ (US); Runli Liang, Mesa, AZ (US); Guangzhong Ma, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 228 days.

(21) Appl. No.: 18/265,057

(22) PCT Filed: Dec. 6, 2021

(86) PCT No.: PCT/US2021/061940
§ 371 (c)(1),
(2) Date: Jun. 2, 2023

(87) PCT Pub. No.: WO2022/125410
PCT Pub. Date: Jun. 16, 2022

(65) Prior Publication Data

US 2024/0118200 A1 Apr. 11, 2024

Related U.S. Application Data

(60) Provisional application No. 63/122,687, filed on Dec. 8, 2020.

(51) Int. Cl.

| | |
|---|---|
| ***G01N 21/43*** | (2006.01) |
| ***G01N 33/542*** | (2006.01) |

(52) U.S. Cl.
CPC .......... *G01N 21/43* (2013.01); *G01N 33/542* (2013.01); *G01N 2021/437* (2013.01)

(58) Field of Classification Search
CPC ............................ G01N 21/553; G01N 21/43
See application file for complete search history.

(56) References Cited

U.S. PATENT DOCUMENTS

| | | | | |
|---|---|---|---|---|
| 4,390,781 | A | 6/1983 | Musha | |
| 2003/0112427 | A1 * | 6/2003 | Ryan | G01N 33/551 356/136 |

(Continued)

FOREIGN PATENT DOCUMENTS

| | | | | |
|---|---|---|---|---|
| CN | 108732132 A | * 11/2018 | | G01N 21/4133 |

OTHER PUBLICATIONS

Š. Bálint, I. Verdeny Vilanova, Á. Sandoval Álvarez, & M. Lakadamyali, Correlative live-cell and superresolution microscopy reveals cargo transport dynamics at microtubule intersections, Proc. Natl. Acad. Sci. U.S.A. 110 (9) 3375-3380, https://doi.org/10.1073/pnas.1219206110 (2013). (Year: 2013).*

(Continued)

*Primary Examiner* — Kara E. Geisel
*Assistant Examiner* — Christina I Xing
(74) *Attorney, Agent, or Firm* — MH2 Technology Law Group, LLP

(57) ABSTRACT

This disclosure describes systems and methods for critical angle reflection (CAR) imaging to quantify molecular binding kinetics on a glass surface in some embodiments. CAR is a label-free method that measures the reflectivity change near a critical angle in response to molecular binding induced refractive index changes on the sensor surface. The sensitivity and dynamic range of CAR is tunable by varying the incident angle of light, which allows for optimizing the (Continued)

100

102 — Contacting a liquid comprising a ligand with a first surface of a substrate functionalized with a receptor, wherein the substrate is optically transparent and wherein a refractive index of the substrate exceeds a refractive index of the liquid 104 — Introducing an incident light into an optical prism toward a second surface of the substrate at an incident angle with respect to a plane perpendicular to the first surface of the substrate, wherein the second surface is opposite the first surface and the incident angle is less than a critical angle defined as $\sin^{-1}(n_a/n_g)$, wherein $n_g$ is the refractive index of the substrate and $n_a$ is the refractive index of the liquid 106 — Assessing a change in intensity of the light reflected at an interface between the liquid and the first surface of the substrate, wherein the change in intensity is responsive to binding of the ligand by the receptor measurement for ligands with different sizes in both biomolecular and cell-based studies.

15 Claims, 19 Drawing Sheets

Specification includes a Sequence Listing.

(56) References Cited

U.S. PATENT DOCUMENTS

| | | | | |
|---|---|---|---|---|
| 2006/0262538 | A1* | 11/2006 | Li | H10H 20/853 257/E33.059 |
| 2007/0231924 | A1 | 10/2007 | Muraishi | |
| 2009/0156427 | A1 | 6/2009 | Zhang et al. | |
| 2011/0039280 | A1* | 2/2011 | Leary | G01N 21/6458 435/7.32 |
| 2012/0244554 | A1* | 9/2012 | Giavazzi | G01N 21/55 435/7.1 |
| 2016/0169873 | A1* | 6/2016 | Tao | G01N 21/77 435/5 |
| 2020/0270560 | A1 | 8/2020 | Kelso et al. | |

OTHER PUBLICATIONS

International Search Report and Written Opinion mailed Feb. 23, 2022 in corresponding International Application No. PCT/US2021/061940, 17 pages.

* cited by examiner

CRITICAL ANGLE REFLECTION IMAGING FOR QUANTIFICATION OF MOLECULAR INTERACTIONS

CROSS-REFERENCE TO RELATED APPLICATIONS

This application is a national stage entry under 35 U.S.C. § 371 of PCT Application No. PCT/US2021/061940 entitled "CRITICAL ANGLE REFLECTION IMAGING FOR QUANTIFICATION OF MOLECULAR INTERACTIONS" filed Dec. 6, 2021, which claims priority to U.S. Provisional Patent Application Ser. No. 63/122,687, filed Dec. 8, 2020, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 2, 2021, is named 0391_0029-PCT-_SL.txt and is 797 bytes in size.

TECHNICAL FIELD

This invention relates to systems and methods for assessing molecular interactions by critical angle reflection imaging.

BACKGROUND

Molecular interactions are ubiquitous in biological systems and important to the understanding of molecular biology and drug discovery. Surface plasmon resonance (SPR) is a widely used label-free technique in pharmaceuticals and research labs for measuring molecular binding kinetics. Owing to the sharp response to the refractive index change on the surface, the high sensitivity of SPR enables the detection of biomolecules, small molecules, viruses, and cells. To generate SPR on the surface, the sensor chip (glass slide) is typically coated with a metal film (often gold), which increases the operation cost. The gold film is not required for glass-based biosensors, such as interferometers, microring and microsphere resonators. However, these sensors are also often made using costly microfabrication techniques. Reflectometry can measure binding kinetics on a cover glass based on detecting the phase shift of reflection light, but due to the instrumentation complexity and moderate sensitivity, it is not as competitive as SPR.

Accordingly, there is a need for cost-effective and sensitive techniques for measuring molecular interactions.

SUMMARY

This disclosure describes systems and methods for critical angle reflection (CAR) imaging to quantify molecular binding kinetics on a glass surface in some embodiments. CAR is a label-free method that measures the reflectivity change near a critical angle in response to molecular binding induced refractive index changes on the sensor surface. The sensitivity and dynamic range of CAR is tunable by varying the incident angle of light, which allows for optimizing the measurement for ligands with different sizes in both biomolecular and cell-based studies. CAR imaging measurements are suitable for small molecule detection, cell-based sensing, and simultaneous fluorescence imaging.

CAR presents several unique features compared to surface plasmon resonance (SPR). For example, the sensitivity of CAR increases with incident angle and can be higher than SPR as the angle approaches the critical angle, allowing CAR to measure small molecules that are challenging for SPR. Also, CAR uses bare cover glass, which is lower in cost and more compatible with fluorescence measurements than gold coated cover glasses used by SPR, allowing simultaneous measurement of binding kinetics and fluorescence or total internal reflection fluorescence (TIRF). CAR also has a longer vertical sensing range than surface plasmon resonance (SPR) due at least in part to deeper light penetration depth at sub-critical angles.

In one aspect, the present disclosure provides a method of quantifying molecular interactions. The method includes contacting a liquid comprising a ligand with a first surface of a substrate functionalized with a receptor, wherein the substrate is optically transparent and wherein a refractive index of the substrate exceeds a refractive index of the liquid. The method also includes introducing an incident light into an optical prism toward a second surface of the substrate at an incident angle with respect to a plane perpendicular to the first surface of the substrate, wherein the second surface is opposite the first surface and the incident angle is less than a critical angle defined as $\sin^{-1}(n_a/n_g)$, wherein $n_g$ is the refractive index of the substrate and $n_a$ is the refractive index of the liquid. In addition, the method also includes assessing a change in intensity of the light reflected at an interface between the liquid and the first surface of the substrate, wherein the change in intensity is responsive to binding of the ligand by the receptor.

In another aspect, the present disclosure provides a method of detecting a ligand in a liquid. The method includes contacting the liquid with a first surface of a substrate, wherein the first surface of the substrate comprises a receptor, wherein the substrate is optically transparent, and wherein a refractive index of the substrate exceeds a refractive index of the liquid. The method also includes introducing an incident light into an optical prism toward a second surface of the substrate at an incident angle with respect to a plane perpendicular to the first surface of the substrate, wherein the second surface is opposite the first surface and the incident angle is less than a critical angle defined as $\sin^{-1}(n_a/n_g)$, wherein $n_g$ is the refractive index of the substrate and $n_a$ is the refractive index of the liquid. In addition, the method also includes measuring a resonance angle shift in the incident light reflected from an interface between the first surface of the substrate and the liquid, which resonance angle shift is indicative of the receptor binding the ligand, thereby detecting the ligand in the liquid.

In another aspect, the present disclosure provides an optical imaging system that includes an optically transparent substrate having a first surface and a second surface opposite the first surface, and an optical prism configured to be coupled to the second surface of the optically transparent substrate. The system also includes a light source configured to introduce collimated light into the optical prism at an incident angle with respect to a plane perpendicular to the second surface of the optically transparent substrate, wherein the incident angle is less than a critical angle defined as $\sin^{-1}(n_a/n_g)$, wherein $n_g$ is a refractive index of the substrate and $n_a$ is a refractive index of the liquid. In addition, the system also includes a detector configured to collect light reflected from an interface between the first surface of the optically transparent substrate and a liquid in contact with the first surface of the optically transparent substrate, and a processor configured to assess a change in intensity of the light reflected at the interface between the liquid and the first surface of the substrate, wherein the change in intensity is responsive to binding of a ligand in the liquid by a receptor on the second surface of the substrate.

In another aspect, the present disclosure provides an optical imaging system that includes an optically transparent substrate having a first surface and a second surface opposite the first surface, wherein the first surface comprises a receptor, and an optical prism configured to be coupled to the second surface of the optically transparent substrate. The system also includes a light source configured to introduce collimated light into the optical prism at an incident angle with respect to a plane perpendicular to the second surface of the optically transparent substrate, wherein the incident angle is less than a critical angle defined as $\sin^{-1}(n_a/n_g)$, wherein $n_g$ is a refractive index of the substrate and $n_a$ is a refractive index of the liquid. The system also includes a detector configured to collect light reflected from an interface between the first surface of the optically transparent substrate and a liquid in contact with the first surface of the optically transparent substrate. In addition, the system also includes a controller that comprises, or is capable of accessing, computer readable media comprising non-transitory computer-executable instructions which, when executed by at least one electronic processor, perform at least: introducing the collimated light from light source into the optical prism at the incident angle, and detecting a resonance angle shift in the light collected by the detector, which resonance angle shift is indicative of the receptor binding a ligand in the liquid.

In some embodiments, the substrate is directly functionalized with the receptor. In some embodiments, the ligand, the receptor, or both comprise a molecule. In some of these embodiments, the molecule comprises a nucleic acid or a protein. In some embodiments, the receptor comprises a cell.

In some embodiments, a sensitivity of the method increases as the incident angle approaches the critical angle. In some embodiments, assessing the change in intensity comprises assessing binding kinetics of the ligand and the receptor. In some embodiments, assessing the change in intensity comprises assessing the intensity with a camera. In some embodiments, the methods further comprise monitoring interaction of the ligand and the receptor in real time. In some embodiments, binding of the ligand by the receptor alters an effective refractive index of the substrate near the first surface of the substrate.

In some embodiments, the methods further comprise fluorescence imaging of the ligand, the receptor, or both. In some embodiments, the incident light comprises visible light or UV light. In some embodiments, the incident light comprises p-polarized light, s-polarized light, non-polarized light, or circularly polarized light. In some embodiments, the substrate is free of a metallic coating. In some embodiments, the incident light is collimated.

The details of one or more embodiments of the subject matter of this disclosure are set forth in the accompanying drawings and the description. Other features, aspects, and advantages of the subject matter will become apparent from the description, the drawings, and the claims.

DEFINITIONS

Figure 1:
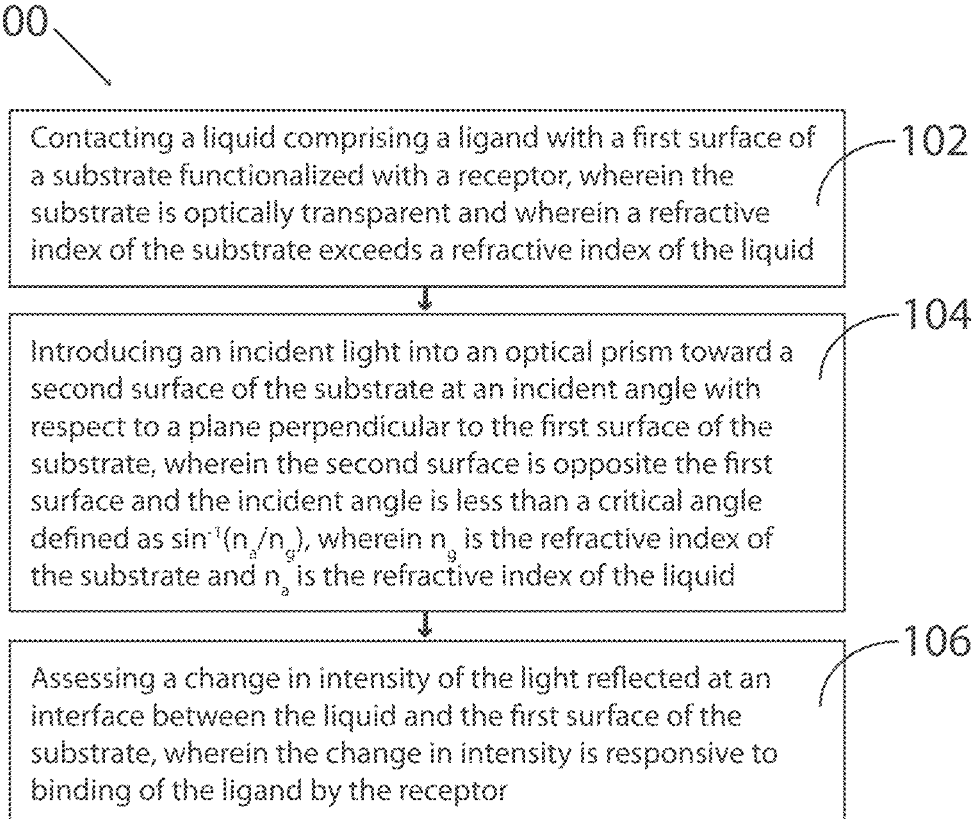
FIG. 1 is a flow chart that schematically shows exemplary method steps of quantifying molecular interactions according to some aspects disclosed herein.

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms “a,” “an,” and “the” include plural references unless the context clearly dictates otherwise. Thus, for example, a reference to “a method” includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and computer readable media, the following terminology, and grammatical variants thereof, will be used in accordance with the definitions set forth below.

Functionalized: As used herein, the term “functionalized” in the context of analyzing molecular interactions on substrates refers to a receptor disposed directly or indirectly on a surface of the substrate (e.g., an optically transparent glass substrate). In some embodiments, receptors are attached to, or otherwise immobilized on, substrate surfaces via a linker moiety or coating. In some embodiments, receptors are displayed on the surfaces of cells that are disposed on a surface of a substrate.

Refractive Index: As used herein, the term “refractive index” refers to a ratio of the speed of light in one medium (e.g., air, glass, or a vacuum) to that in another medium. In some embodiments, a refractive index of a given substrate (e.g., an optically transparent glass substrate) exceeds a refractive index of a liquid comprising a ligand being assessed.

Resonance Angle: As used herein, the term “resonance angle” in the context of optically analyzing molecular interactions on substrates refers to an angle of incident light at which resonance occurs. In some embodiments, molecular interactions are assessed by detecting changes or shifts in resonance angles.

DETAILED DESCRIPTION

This disclosure describes critical angle reflection (CAR) imaging systems and methods for measuring the molecular interactions on bare glass surfaces. CAR imaging systems include some features of surface plasmon resonance (SPR) systems. In CAR, the sensor chip is a bare glass (e.g., rather than a gold coated cover glass), and the incident light can be either p-polarized, or s-polarized, or non-polarized. The incident light is set at slightly below the critical angle. To perform measurements, the glass surface is functionalized with receptor molecules to capture the ligands in the solution, and upon ligand binding, the refractive index near the surface changes, leading to a change in the reflected light intensity or a change or shift in resonance angle. By measuring the intensity or resonance angle change with a camera, the receptor-ligand interaction can be monitored in real-time.

To illustrate, FIG. 1 is a flow chart that schematically shows exemplary method steps of quantifying molecular interactions according to some aspects disclosed herein. As shown, method 100 includes contacting a liquid comprising a ligand with a first surface of a substrate functionalized with a receptor, wherein the substrate is optically transparent and wherein a refractive index of the substrate exceeds a refractive index of the liquid (step 102). Method 100 also includes introducing an incident light into an optical prism toward a second surface of the substrate at an incident angle with respect to a plane perpendicular to the first surface of the substrate, wherein the second surface is opposite the first surface and the incident angle is less than a critical angle defined as $\sin^{-1}(n_a/n_g)$, wherein $n_g$ is the refractive index of the substrate and $n_a$ is the refractive index of the liquid (step 104). In addition, method 100 also includes assessing a change in intensity of the light reflected at an interface between the liquid and the first surface of the substrate, wherein the change in intensity is responsive to binding of the ligand by the receptor (step 106).

Figure 2:
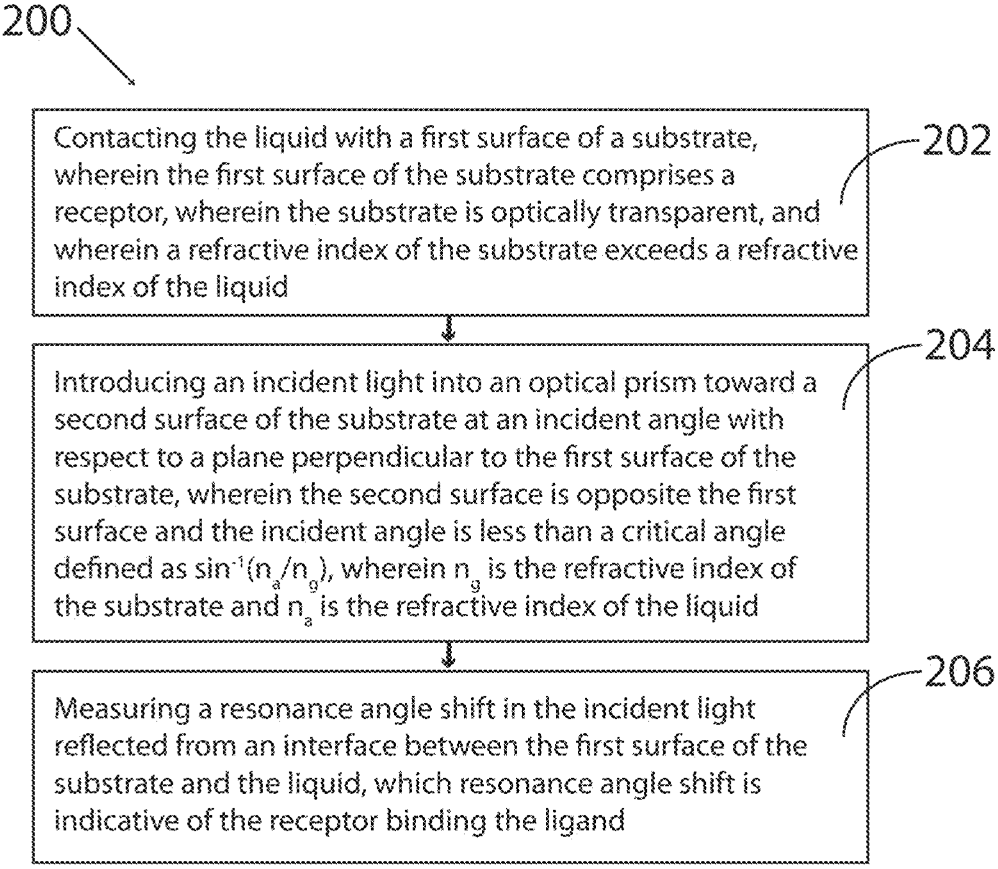
FIG. 2 is a flow chart that schematically shows exemplary method steps of detecting a ligand in a liquid according to some aspects disclosed herein.

To further illustrate, FIG. 2 is a flow chart that schematically shows exemplary method steps of detecting a ligand in a liquid according to some aspects disclosed herein. As shown, method 200 includes contacting the liquid with a first surface of a substrate, wherein the first surface of the substrate comprises a receptor, wherein the substrate is optically transparent, and wherein a refractive index of the substrate exceeds a refractive index of the liquid (step 202). Method 200 also includes introducing an incident light into an optical prism toward a second surface of the substrate at an incident angle with respect to a plane perpendicular to the first surface of the substrate, wherein the second surface is opposite the first surface and the incident angle is less than a critical angle defined as $\sin^{-1}(n_a/n_g)$, wherein $n_g$ is the refractive index of the substrate and $n_a$ is the refractive index of the liquid (step 204). In addition, method 200 also includes measuring a resonance angle shift in the incident light reflected from an interface between the first surface of the substrate and the liquid, which resonance angle shift is indicative of the receptor binding the ligand (step 206).

The detection principle of CAR with p- or s-polarized light can be described by Fresnel equation. When a p polarized light is introduced into a glass prism at an incident angle 9; and reflected at the interface between the glass and the aqueous solution, as shown in FIG. 4*a*, the reflectivity (power reflection coefficient) $R_p$ is given by $$R_p = \left| \frac{n_g\sqrt{1-\left(\frac{n_g}{n_a}\sin\theta_i\right)^2} - n_a\cos\theta_i}{n_g\sqrt{1-\left(\frac{n_g}{n_a}\sin\theta_i\right)^2} + n_a\cos\theta_i} \right|^2 \quad (1)$$

where $n_g$ is the refractive index of glass, and $n_a$ is refractive index of aqueous solution. $R_p$ increases with the incident angle, and reaches maximum value of 1 at critical angle $\theta_c$, where $$\theta_c = \sin^{-1}\left(\frac{n_a}{n_g}\right) \quad (2)$$

Figures 4A, 4B, 4C, 4D, 4E:
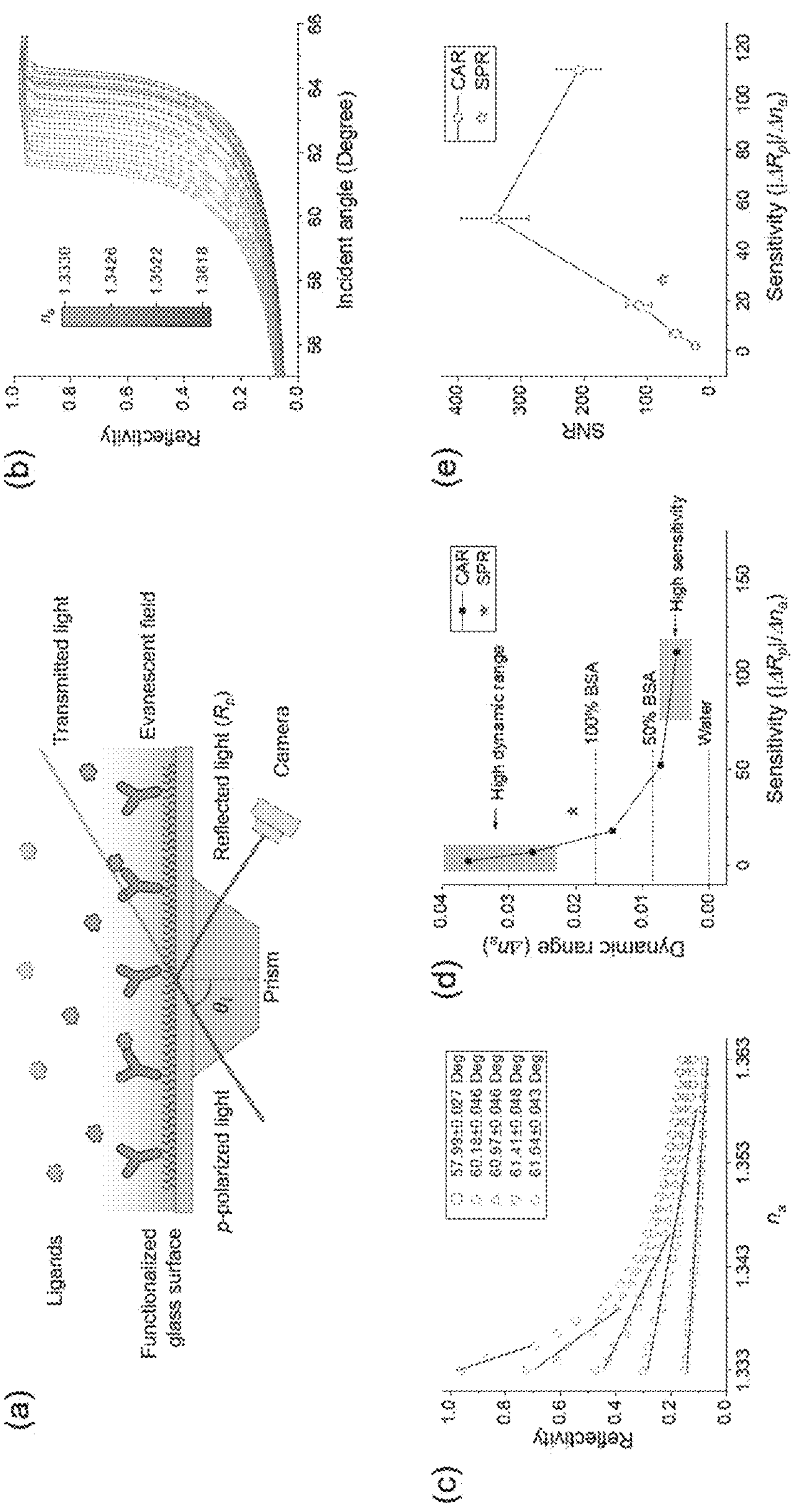
FIG. 4. Detection principle of CAR. (a) Experimental setup and surface chemistry. A protein functionalized cover glass is placed on a prism-based SPR imaging setup with index matching oil. The incident angle $\theta_i$ of a collimated laser light is set at slightly below the critical angle. Upon ligands binding to the proteins, the intensity of the reflected light changes and is detected by a camera. (b) Reflectivity change as a function of incident angle. In SPR, p-polarized light is used for the measurement. The refractive index ($n_a$) on the surface is adjusted by serially adding ethanol to water to make $n_a$ ranges from 1.3330 (pure water) to 1.3630 (50% ethanol in water). (c) Reflectivity as a function of n at five representative incident angles with data obtained from (b). The solid lines show the linear regions (defined by $R^2>0.97$, where $R^2$ is the coefficient of determination) of the curves. (d) Tunable sensitivity and dynamic range of CAR. The black dots show the sensitivity and dynamic range determined at the five representative angles in (c), where the sensitivity and dynamic range are the slope and the range of the linear regions, respectively. The star marks the sensitivity and dynamic range of SPR, which is not adjustable. To facilitate comparison, the refractive index change induced by the binding of a full layer of BSA (100% BSA), half layer of BSA (50% BSA), and pure water (Water) are marked by the dashed lines. (e) Signal-to-noise ratio of SPR and CAR at the five representative angles. Noise is defined as 1 minute of root mean square of baseline signal.
Figure 10A:
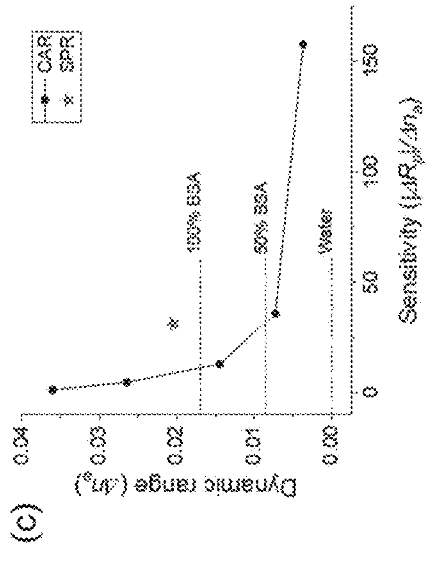
FIG. 10. Simulation results of CAR with p-polarized incident light. (a) Relationship between reflectivity and incident angle at different aqueous solution refractive indices ($n_a$). (b) Reflectivity vs. $n_a$ at five representative incident angles. The black lines are fittings of the linear regions ($R^2$>0.97). (c) Sensitivity and dynamic range of CAR at the five representative angles (black dots). Sensitivity and dynamic range are determined by the slope and the linear range of the black lines in (b). The grey star marks the theoretical sensitivity and dynamic range of SPR. The simulation is shown in FIG. 11.
Figure 10B:
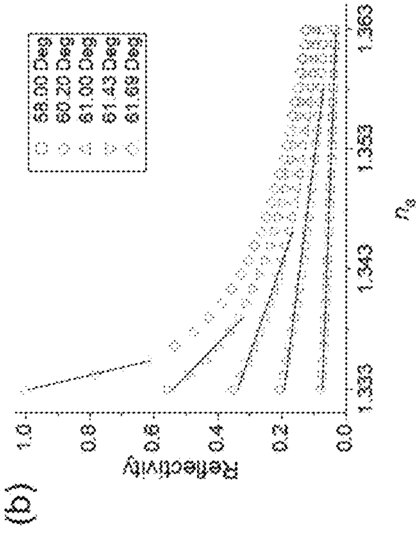
Figure 10C:
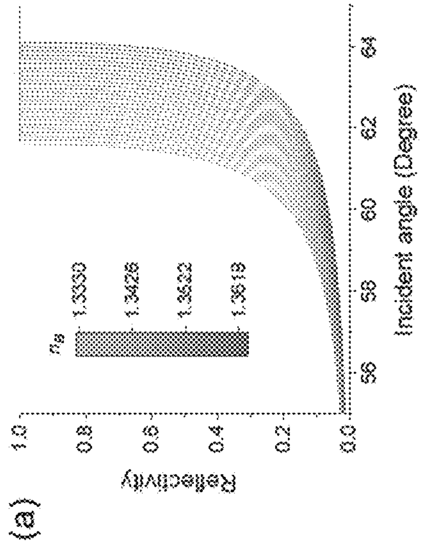
Figures 11A, 11B, 11C, 11D:
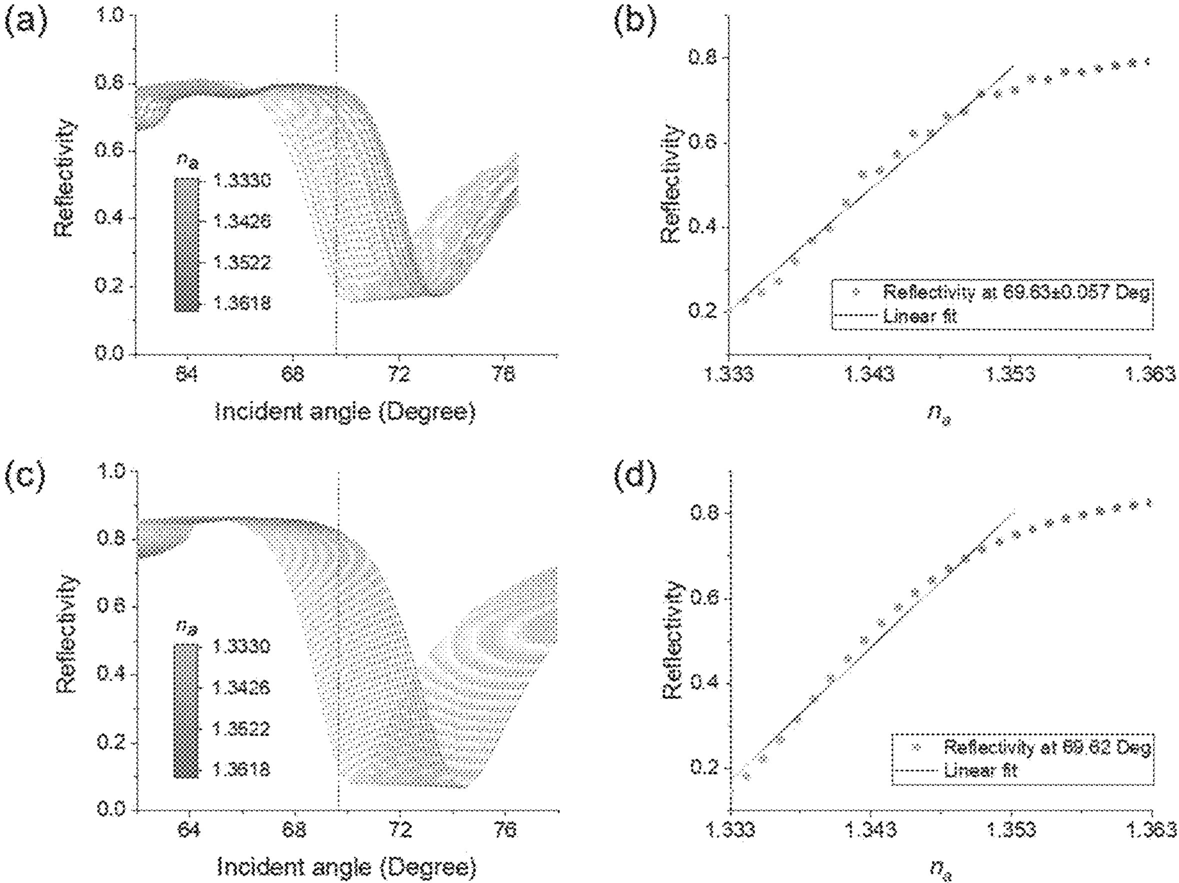
FIG. 11. Experimental and simulated SPR responses. (a) Measured reflectivity as a function of incident angle at different aqueous solution refractive indices ($n_a$). (b) Reflectivity vs. $n_a$ at 69.63 degrees (marked by the vertical dash line in a). The black line is fitting of the linear region ($R^2$>0.97). The sensitivity and the dynamic range of SPR are determined by the slope and the linear range of the black line. (c) Simulated SPR reflectivity at different incident angles and $n_a$. (d) Reflectivity vs. $n_a$ plot at 69.62 degrees (marked by the vertical dash line in c) obtained from the simulated data in c. The black line is fitting of the linear region ($R^2$>0.97), from which the theoretical sensitivity and dynamic range are calculated.

Scanning $\theta_i$ from below to above $\theta_c$ shows that $R_p$ increases faster as $\theta_i$ approaches $\theta_c$ and finally reaches total internal reflection at $\theta_c$ (FIG. 4*b*). The sensitivity of CAR arises from the rapid reflectivity change ($\Delta R_p$) near $\theta_c$ caused by the refractive index change in the aqueous solution near glass surface ($\Delta n_a$) due to molecular binding. Since most of molecules have a higher refractive index than water, a molecular binding event at the glass surface usually increases the effective refractive index of aqueous solution above the glass surface ($\Delta n_a>0$) and results in right-shift of the curve, which lowers the reflectivity ($\Delta R_p<0$) if $\theta_i$ is fixed at an angle slightly lower than $\theta_c$. For a given $\Delta n_\alpha$, $|\Delta R_p|$ becomes larger as the $\theta_i$ gets closer to $\theta_c$. The experimental results were verified by simulation (FIG. 10). This feature allows the sensitivity ($|\Delta R_p|/\Delta n_a$) to be tuned by changing $\theta_i$ (FIG. 4*c*). In contrast, the sensitivity of SPR is fixed for $\theta_i$ in the normal measurement range (FIG. 11).

Figure 20A:
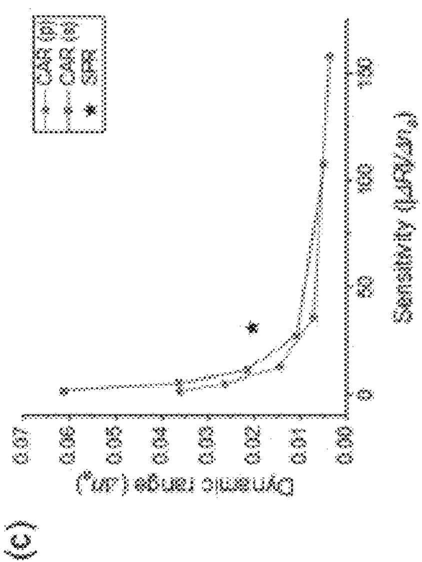
FIG. 20. Simulation results of CAR with s-polarized incident light. (a) Relationship between reflectivity and incident angle at different aqueous solution refractive indices ($n_a$) for s-polarized light. (b) Reflectivity vs. $n_a$ at five representative incident angles for s-polarized light. The black lines are fittings of the linear regions ($R^2>0.97$). (c) Sensitivity and dynamic range of CAR with s-polarization (CAR(s)) and p-polarization (CAR(p)) at the five representative angles. The star marks the theoretical sensitivity and dynamic range of SPR. The CAR(p) and SPR data are adopted from FIG. 101C.
Figure 20B:
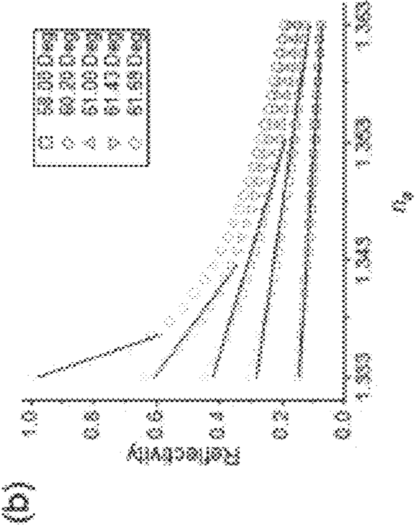
Figure 20C:
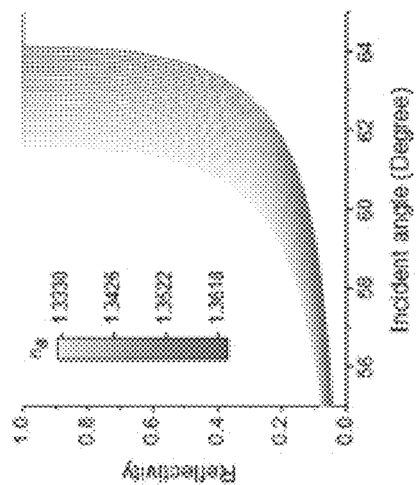

Similar results can be obtained using s-polarized incident light for CAR (FIG. 20) with the following equation.

$$R_s = \left| \frac{n_a\sqrt{1-\left(\frac{n_g}{n_a}\sin\theta_i\right)^2} - n_g\cos\theta_i}{n_a\sqrt{1-\left(\frac{n_g}{n_a}\sin\theta_i\right)^2} + n_g\cos\theta_i} \right|^2 \quad (3)$$

A CAR imaging system includes an optically transparent substrate having a first surface and a second surface opposite the first surface, and an optical prism configured to be coupled to the second surface of the optically transparent substrate. As used herein, "optically transparent" generally refers to a light transmission or total transmittance of at least about 85% or at least about 90% as measured according to ASTM D1003. The CAR imaging system further includes a light source configured to introduce collimated light into the optical prism at an incident angle with respect to a plane perpendicular to the second surface of the optically transparent substrate. The light source can provide visible or UV light. The incident angle is less than a critical angle defined as $\sin^{-1}(n_a/n_g)$, wherein $n_g$ is a refractive index of the substrate and $n_a$ is a refractive index of the liquid. The CAR imaging system also includes a detector configured to collect light reflected from an interface between the first surface of the optically transparent substrate and a liquid in contact with the first surface of the optically transparent substrate. In one example, the detector is a camera. In some embodiments, the CAR imaging system includes a processor configured to assess a change in intensity of the light reflected at the interface between the liquid and the first surface of the substrate, wherein the change in intensity is responsive to binding of a ligand in the liquid by a receptor on the second surface of the substrate. Exemplary systems are described further herein.

Assessing (e.g., quantifying) molecular interactions with the CAR imaging system includes contacting a liquid including a ligand with a first surface of a substrate functionalized with a receptor. The substrate is optically transparent, and a refractive index of the substrate exceeds a refractive index of the liquid. Collimated light is introduced into an optical prism toward a second surface of the substrate at an incident angle with respect to a plane perpendicular to the first surface of the substrate. This incident light can be p-polarized light, s-polarized light, non-polarized light, or circularly polarized light. The second surface of the optically transparent substrate is opposite the first surface of the optically transparent substrate. The incident angle is less than a critical angle defined as $\sin^{-1}(n_a/n_g)$, wherein $n_g$ is the refractive index of the substrate and $n_a$ is the refractive index of the liquid. A sensitivity typically increases as the incident angle approaches the critical angle. When a ligand in the liquid binds to the receptor on the first surface of the substrate, an effective refractive index of the substrate near the first surface of the substrate is altered, and the intensity of the light reflected at the interface between the liquid and the first surface of the substrate changes. As described herein, assessing this change in intensity allows quantification of interactions (e.g., in real time) between the ligand and the receptor.

In some embodiments, the substrate is glass. The substrate is directly functionalized with the receptor. That is, the receptor is directly bound to the optically transparent substrate rather than an opaque (e.g., metallic) coating on the substrate. The ligand, the receptor, or both can be molecules (e.g., a small molecule, a nucleic acid, or a protein). In some cases, the receptor is a cell. Assessing the change in intensity can include collecting the reflected light with a detector (e.g., a camera). From change in intensity, molecular interactions between the ligand and the receptor (e.g., binding kinetics) can be assessed.

Figure 3:
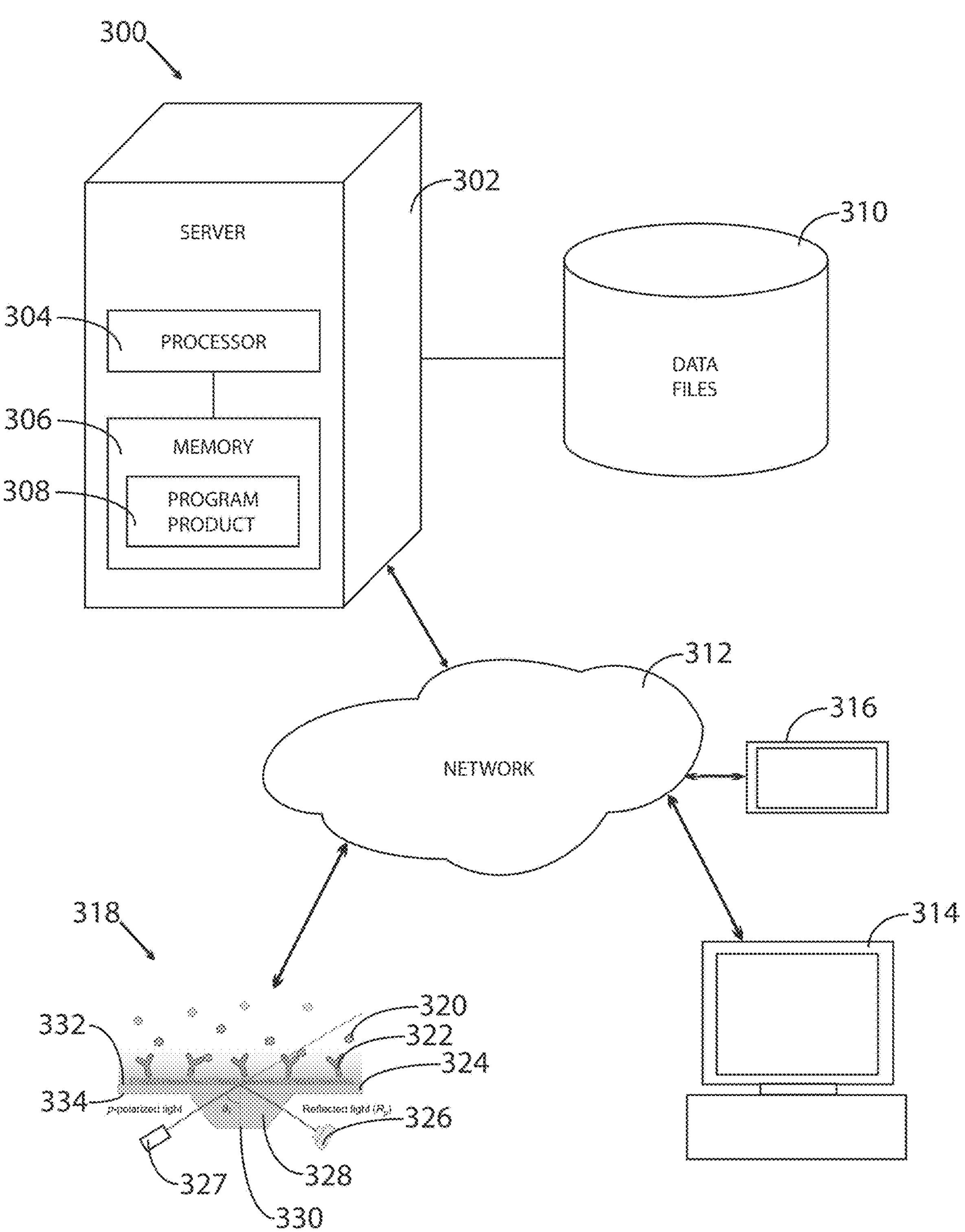
FIG. 3 is a schematic diagram of an exemplary system suitable for use with certain aspects disclosed herein.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 3 provides a schematic diagram of an exemplary system suitable for use with implementing at least aspects of the methods disclosed in this application. As shown, system 300 includes at least one controller or computer, e.g., server 302 (e.g., a search engine server), which includes processor 304 and memory, storage device, or memory component 306, and one or more other communication devices 314, 316, (e.g., client-side computer terminals, telephones, tablets, laptops, other mobile devices, etc. (e.g., for receiving molecular interaction data sets or results, etc.) in communication with the remote server 302, through electronic communication network 312, such as the Internet or other internetwork. Communication devices 314, 316 typically include an electronic display (e.g., an internet enabled computer or the like) in communication with, e.g., server 302 computer over network 312 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 300 also includes program product 308 (e.g., for detecting a ligand as described herein) stored on a computer or machine readable medium, such as, for example, one or more of various types of memory, such as memory 306 of server 302, that is readable by the server 302, to facilitate, for example, a guided search application or other executable by one or more other communication devices, such as 314 (schematically shown as a desktop or personal computer). In some aspects, system 300 optionally also includes at least one database server, such as, for example, server 310 associated with an online website having data stored thereon (e.g., entries corresponding to molecular interaction data, etc.) searchable either directly or through search engine server 302. System 300 optionally also includes one or more other servers positioned remotely from server 302, each of which are optionally associated with one or more database servers 310 located remotely or located local to each of the other servers. The other servers can beneficially provide service to geographically remote users and enhance geographically distributed operations.

As understood by those of ordinary skill in the art, memory 306 of the server 302 optionally includes volatile and/or nonvolatile memory including, for example, RAM, ROM, and magnetic or optical disks, among others. It is also understood by those of ordinary skill in the art that although illustrated as a single server, the illustrated configuration of server 302 is given only by way of example and that other types of servers or computers configured according to various other methodologies or architectures can also be used. Server 302 shown schematically in FIG. 3, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 300. As also understood by those of ordinary skill in the art, other user communication devices 314, 316 in these aspects, for example, can be a laptop, desktop, tablet, personal digital assistant (PDA), cell phone, server, or other types of computers. As known and understood by those of ordinary skill in the art, network 312 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 308 is optionally in the form of microcode, programs, cloud computing format, routines, and/or symbolic languages that provide one or more sets of ordered operations that control the functioning of the hardware and direct its operation. Program product 308, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 308 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 308 is optionally copied from the computer-readable medium to a hard disk or a similar intermediate storage medium. When program product 308, or portions thereof, are to be run, it is optionally loaded from their distribution medium, their intermediate storage medium, or the like into the execution memory of one or more computers, configuring the computer(s) to act in accordance with the functionality or method of various aspects disclosed herein. All such operations are well known to those of ordinary skill in the art of, for example, computer systems.

In some aspects, program product 308 includes non-transitory computer-executable instructions which, when executed by electronic processor 304, perform at least: introducing the collimated light from light source into the optical prism at the incident angle, and detecting a resonance angle shift in the light collected by the detector, which resonance angle shift is indicative of the receptor binding a ligand in the liquid.

Typically, molecular interaction data is obtained from liquid samples using device 318. As shown, device 318 includes optically transparent substrate 324 having first surface 332 and second surface 334 opposite first surface 332. First surface 332 comprises receptors 322 (e.g., antibodies or other binding moieties), which bind ligands 320. Optical prism 328 is coupled to second surface 334 of optically transparent substrate 324. Device 318 also includes light source 327 configured to introduce collimated light into optical prism 328 at an incident angle ($\Theta_{i6}$) with respect to plane 330 perpendicular to second surface 334 of optically transparent substrate 324. In addition, device 318 also includes detector 326 (e.g., a camera) configured to collect light reflected from an interface between first surface 332 of optically transparent substrate 324 and a liquid in contact with first surface 332 of optically transparent substrate 324.

Figures 12A, 12B, 12C, 12D:
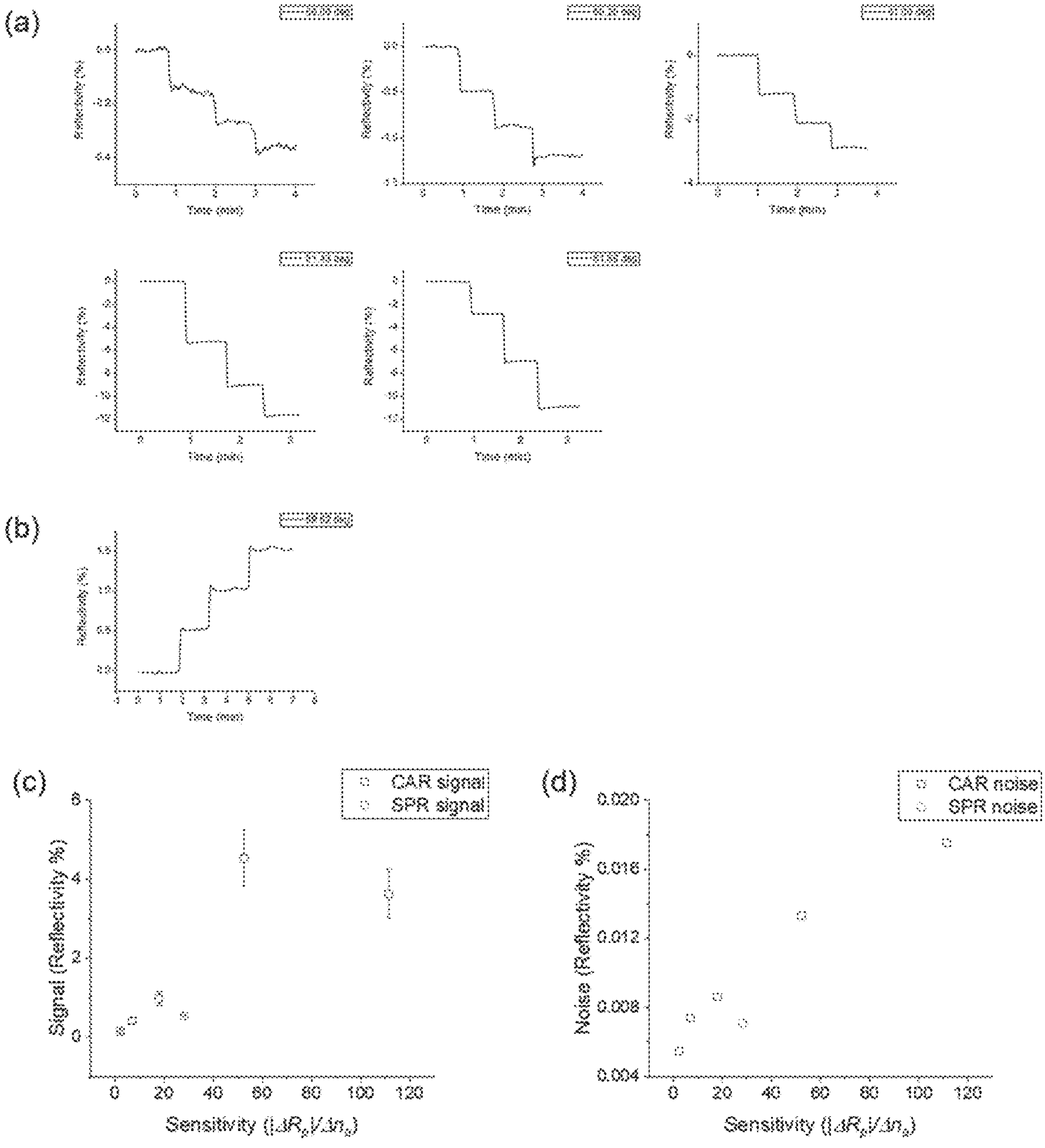
FIG. 12. Measuring the SNR for CAR and SPR. (a) Determining the SNR for CAR at five representative angles. 1% ethanol (final concentration) is added to water for three times, which leads to three reflectivity drops. The average value of the three responses is defined as the signal, and the standard deviation of the baseline (over 1 minute) is defined as the noise. (b) Determining the SNR for SPR. 1% ethanol (final concentration) is added to water for three times. The signal and noise are calculated the same way as in (a). (c) Signal of CAR and SPR. The error bar represents the standard deviation of three measurements. (d) Noise of CAR and SPR.

EXAMPLE: Critical Angle Reflection Imaging for Quantification of Molecular Interactions on Glass Surface To evaluate the performance of CAR as a sensing method, its sensitivity and dynamic range were compared with those of SPR using the same instrument. The sensitivity and dynamic range are defined as the absolute value of slope and linear range of a plot of $R_p$ vs. $n_a$ at given angles (FIG. 4*c* and FIG. 11), respectively. The results for CAR and SPR are plotted in FIG. 4*d*. At low angles, CAR presents low sensitivity, but the dynamic range can be 2 times greater than SPR. At high angles, CAR is 5 times more sensitive than SPR, but the dynamic range is 4 times lower. The reduced dynamic range at high angles is still sufficient to measure the binding of medium sized proteins. For example, bovine serum albumin (BSA, 66 kDa) at up to 25% surface coverage. In between the low and the high angles, CAR has similar sensitivity and dynamic range as SPR. We also measured the signal-to-noise ratio (SNR) of CAR (FIG. 4*e*). The incident light was parked at five representative angles, and 1% ethanol was added to water to generate a refractive index increase (FIG. 12). The ethanol induced reflectivity change and baseline fluctuation were defined as the signal and noise, respectively. The maximum SNR of CAR is ~5 times higher than SPR, suggesting CAR is more sensitive to smaller molecules than SPR.

Biomolecule Detection

Figures 5A, 5B, 5C, 5D, 5E, 5F:
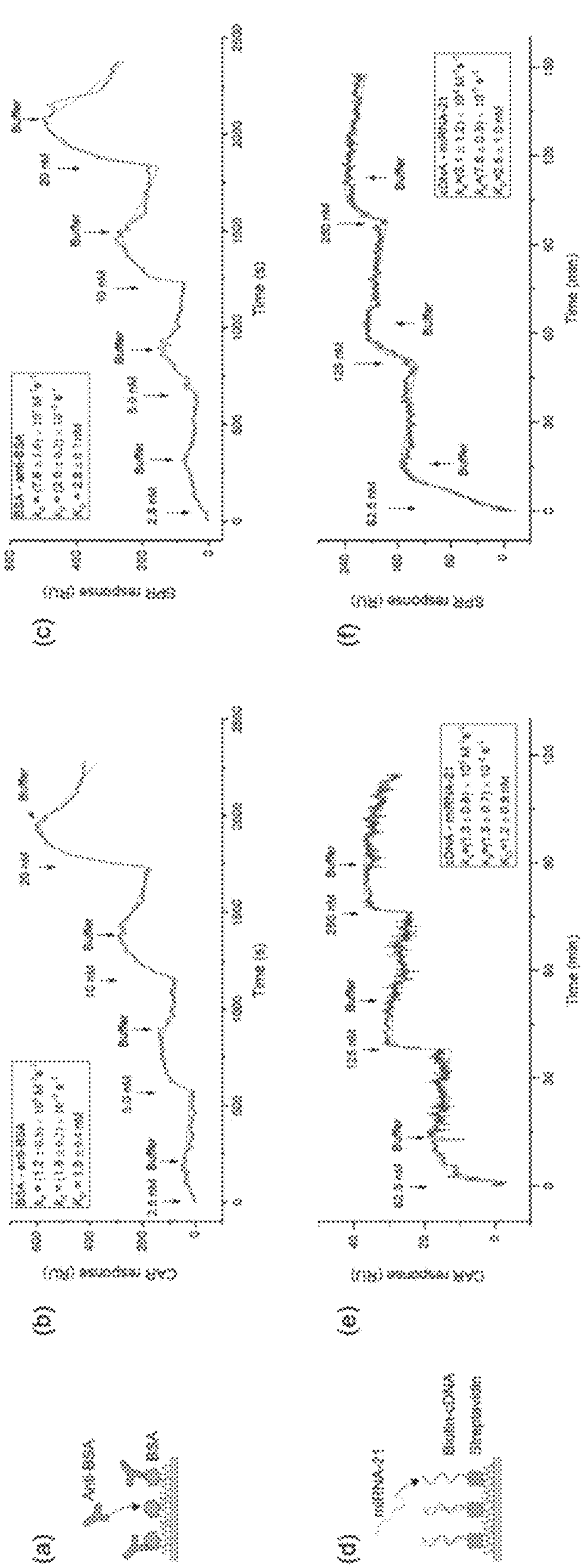
FIG. 5. (a) Anti-BSA binding to BSA. BSA is immobilized on a glass or gold surface for CAR or SPR measurements. (b) Measuring anti-BSA—BSA binding kinetics with CAR. The incident angle was parked at 61.1 degrees with a sensitivity of 25 $RIU^{-1}$. Anti-BSA with different concentrations and buffer were sequentially flowed over the BSA coated surface. The CAR response (black curve) was fitted to the first order of kinetics (grey curve). Note that 1 RU=$10^6$ RIU=1 $pg/mm^2$ of mass density. (c) Measuring anti-BSA—BSA binding kinetics with SPR. The experimental conditions were the same as the CAR measurement. (d) miRNA-21 binding to cDNA. The biotinylated cDNA was immobilized on a streptavidin coated glass or gold surface via streptavidin-biotin conjugation. The miRNA-21—cDNA binding was measured with CAR (e) and SPR (f), and the curves (black) were fitted to the first order of kinetics (grey curves). The CAR incident angle was parked at 61.4 degrees with a sensitivity of 50 $RIU^{-1}$.

To demonstrate the capability of CAR in measuring binding kinetics, the binding of bovine serum albumin antibody (anti-BSA) to bovine serum albumin (BSA) was measured. Anti-BSA and BSA can be used as a model binding pair in SPR (see, e.g., FIG. 5*a*). BSA was immobilized on the surface of a cover glass. Because anti-BSA is a large biomolecule (150 kDa), the CAR sensitivity was tuned to medium sensitivity (~25 $RIU^{-1}$, close to SPR) by parking the incident angle at 61.1 degrees. In the experiment, different concentrations of anti-BSA were serially injected over the BSA coated surface. Binding of anti-BSA to BSA increased the refractive index on the sensing surface. After anti-BSA binding in each cycle, buffer was introduced to the surface to induce the dissociation of anti-BSA from BSA. By fitting the CAR response curves to first order binding kinetics, the association rate constant $k_a$, dissociation rate constant $k_d$, and equilibrium constant $K_D$ were determined to be $(1.2\pm0.5)\times10^6$ $M^{-1}s^{-1}$, $(1.8\pm0.2)\times10^{-3}$ $s^{-1}$, and 1.5±0.4 nM, respectively (FIG. 5*b*). To validate the results, the binding pair was measured again with SPR on a gold surface modified with BSA. By fitting the binding curves (FIG. 5*c*), the kinetic constants are determined, with $k_a=(7.6\pm1.6)\times10^5$ $M^{-1}s^{-1}$, $k_d=(2.0\pm0.2)\times10^{-3}$ $s^{-1}$, and $K_D=2.8\pm0.7$ nM. The kinetic constants obtained from CAR and SPR were close, suggesting the accuracy of CAR as a tool for binding kinetics measurements.

Figures 6A, 6B, 6C, 6D, 6E, 6F, 6G:
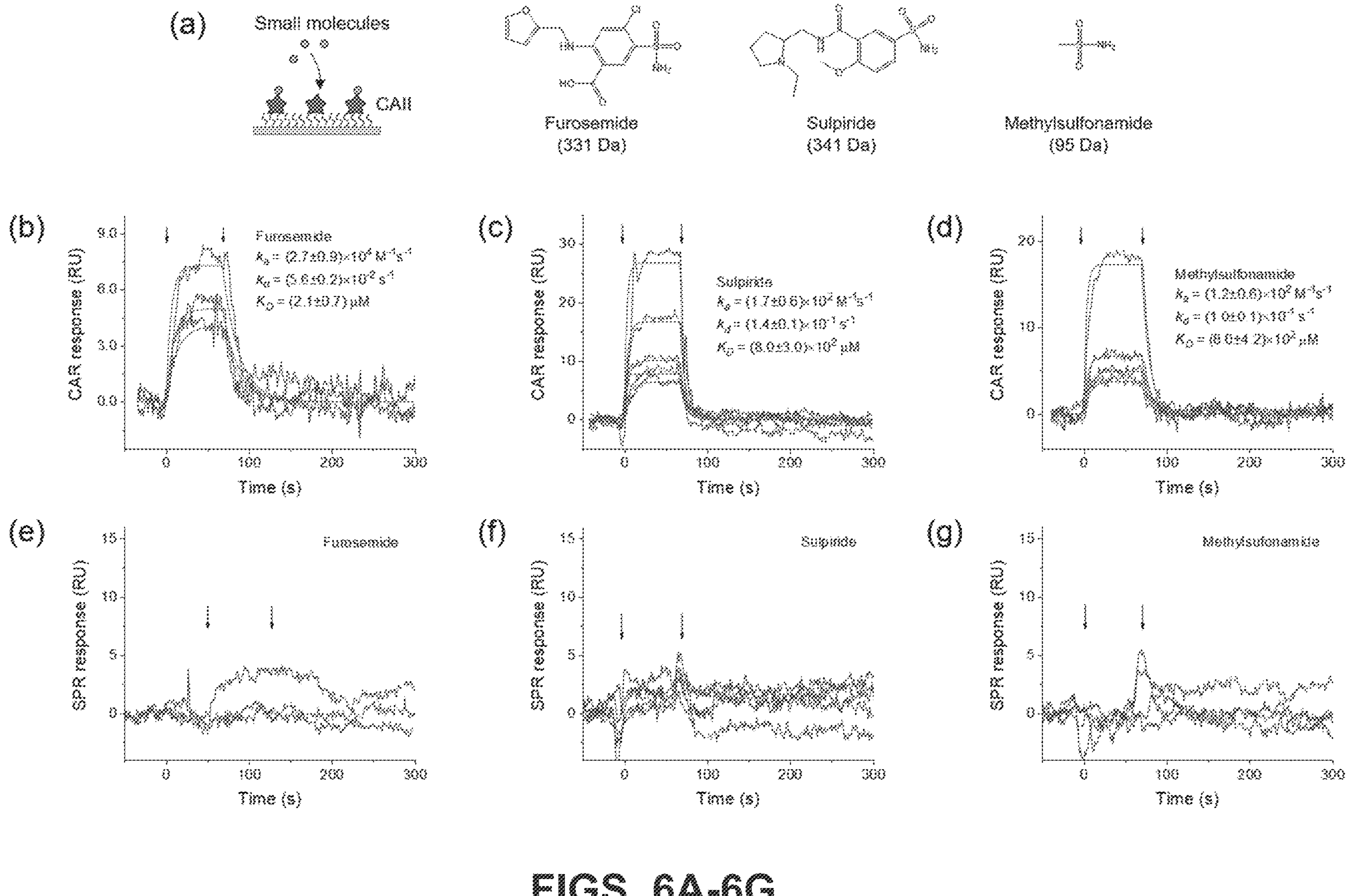
FIG. 6. Measuring the binding kinetics of small molecule ligands to CAII. (a) CAII was immobilized on glass for CAR and gold surface for SPR measurements. Three different small molecules, furosemide (331 Da), sulpiride (341 Da), and methylsulfonamide (95 Da), were flowed over the CAII functionalized chip. (b-d) CAR response curves for furosemide, sulpiride, and methylsulfonamide binding (black curves). The incident angle was parked at 61.6 degrees with a sensitivity of 112. The two arrows mark the starting point of association and dissociation, respectively. The grey curves are global fittings of the data to the first order binding kinetics. Furosemide concentrations: 938 nM, 1.88 μM, and 3.75 μM; Sulpiride concentrations: 62.5 μM, 125 μM, 250 μM, 500 μM, and 1 mM; Methylsulfonamide concentrations: 312 μM, 625 μM, 1.25 mM, and 2.50 mM. (e-g) Same interactions were measured with SPR but no clear response was observed. The CAII surface coverages were 6.5% and 5.8% for the gold and the glass surfaces, respectively.

As an additional example, the binding of a nucleic acid, microRNA-21 (miRNA), which is a biomarker for various cancers, to its complementary DNA (cDNA) was measured. The molecular weight of miRNA-21 is 7 kDa, much smaller than proteins, so $\theta_i$ was set at a higher angle (61.4 degrees) to increase the sensitivity to ~50 $RIU^{-1}$. The glass surface was first modified with streptavidin, and then biotinylated cDNA was immobilized on the surface via biotin-streptavidin conjugation (FIG. 5*d*). miRNA-21 and buffer were flowed sequentially to the surface to measure the association and dissociation of miRNA. The CAR response was recorded, and the kinetic constants were obtained by fitting the response curves (FIG. 5*e*). The same interaction was also measured with SPR, and the results are shown in FIG. 6*f*.

In principle, the SNR of CAR in the experiment should be several times higher than SPR (FIG. 4*e*), but the results were not as expected. One reason was because of the difference in cDNA surface coverage on glass and gold. When the immobilization of streptavidin and biotinylated cDNA on glass and gold using CAR and SPR, respectively, were monitored, it was found that the cDNA coverage on gold was 3.6 times as much as that on glass (FIG. 13). Another reason for the unexpected noise in CAR was that the streptavidin sample had some small aggregates that could not be tightly immobilized on the surface, which were washed off and tumbling around the surface in the following miRNA measurement. This phenomenon was only observed in CAR because CAR is more sensitive to particles in bulk solution.

Small Molecule Detection

Figures 14A, 14B:
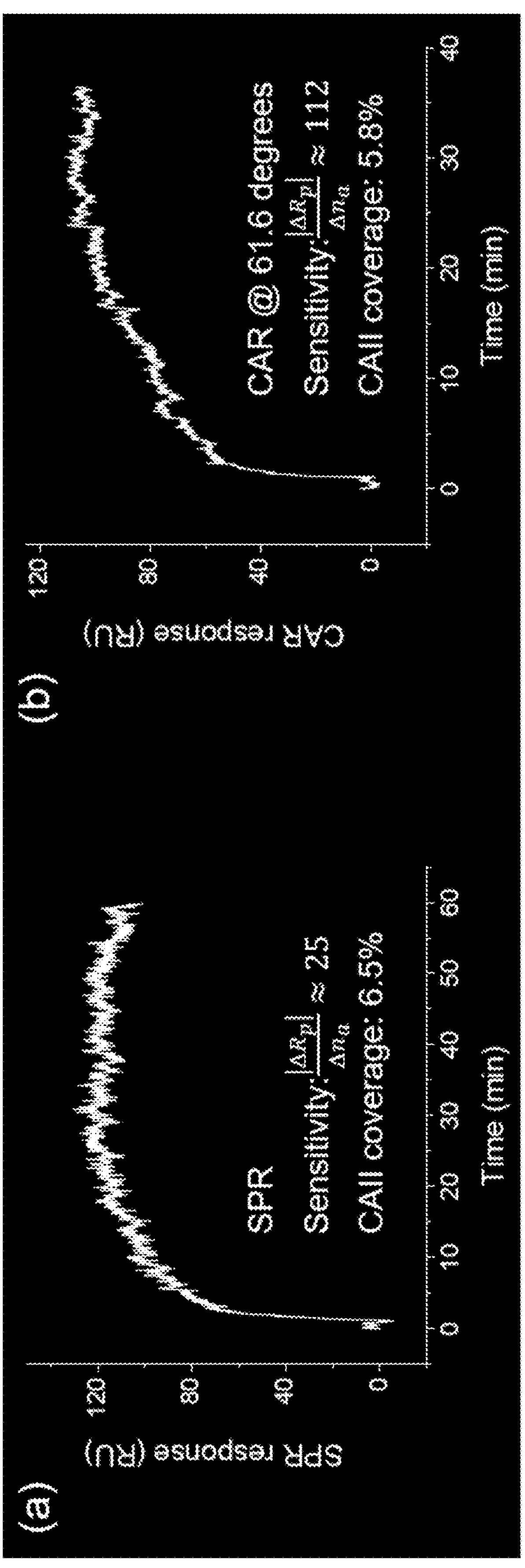
FIG. 14. Surface coverage of CAII on gold and glass surfaces. CAII immobilization process is monitored by SPR (a) and CAR (b). For CAR measurement, the incident angle is parked at 61.6 degrees, which has a sensitivity of ~112 $RIU^{-1}$. The coverage is estimated to be 6.5% and 5.8% on gold and glass surfaces, respectively. 6 nm is used as the diameter of CAII molecules for the coverage estimation.

At higher incident angle close to the critical angle, the enhanced sensitivity and SNR enable CAR to measure smaller molecules that are challenging for SPR. To address this advantage, the interaction between carbonic anhydrase II (CAII) and its small molecule ligands: furosemide (331 Da), sulpiride (341 Da), and methylsulfonamide (95 Da) were measured (FIG. 6*a*). CAII is an enzyme responsible for the catalysis of $CO_2$ hydration, and is found to be related to glaucoma, altitude sickness, obesity, and tumor growth. To perform the measurement, $\theta_i$ was set at 61.6 degrees with a sensitivity of 112 $RIU^1$. CAII was immobilized on a glass surface at 5.8% coverage (FIG. 14), and the small molecules were flowed over the surface. The binding of each small molecule ligand was measured at several different concentrations and globally fitted to the first order kinetics. The results are shown in FIGS. 6*b-d*. The small molecules were also measured with SPR on a gold surface with 6.5% CAII coverage (FIG. 14) using the same experimental conditions, but no obvious signal could be found (FIGS. 6*e-g*). Both the glass surface and the gold surface used in this work were modified with a monolayer of protein receptors for fair comparison.

Modifying a three-dimensional matrix such as dextran can further improve the density of the receptors and hence mass change per unit area upon ligand binding. Previous studies show that the same interactions can be measured with SPR using a dextran coated gold surface, however, the kinetic rate constants were up to 20 times faster than our CAR results. To investigate the discrepancy, the diffusion within the sample delivery system was checked, because slow sample diffusion to the sensor surface can distort the binding curve and lead to false slower kinetics. The sample diffusion time was examined by flowing in 1% ethanol solution (FIG. 15), which ideally should generate a sudden change in reflectivity. In reality, the diffusion time is about 5 s, but still much faster than the time scale of association (~30 s, FIGS. 6*b-d*). Therefore, it is not likely that the kinetics is slowed down by diffusion. Also, by fitting the equilibrium state (FIG. 16) which is not affected by diffusion, $K_D$ is determined to be 782 μM and 1.1 mM for sulpiride and methylsulfonamide, consistent with the real-time values. Based on the above analysis, the measured kinetic constants are believed to be real, and the discrepancy from literature value could be due to difference of surface chemistries and CAII protein sources.

CAR Imaging of Glycoprotein—Lectin Interaction on Cells

In some cases, SPR imaging can be used for measuring the binding kinetics between cell membrane protein and ligand directly on the cells without protein extraction and purification. CAR imaging is also capable of cell-based measurement. Wheat germ agglutinin (WGA) was used as an example. Its interaction with glycoproteins on HeLa cells was measured. WGA is a lectin that can specifically bind to N-acetylglucosamine structures in the sugar chain of glycoproteins. Investigating the interactions between lectin and glycoprotein is important for understanding the role of glycoprotein in many biological processes, including cell recognition, adhesion, growth and differentiation.

Figures 7A, 7B, 7C, 7D, 7E, 7F:
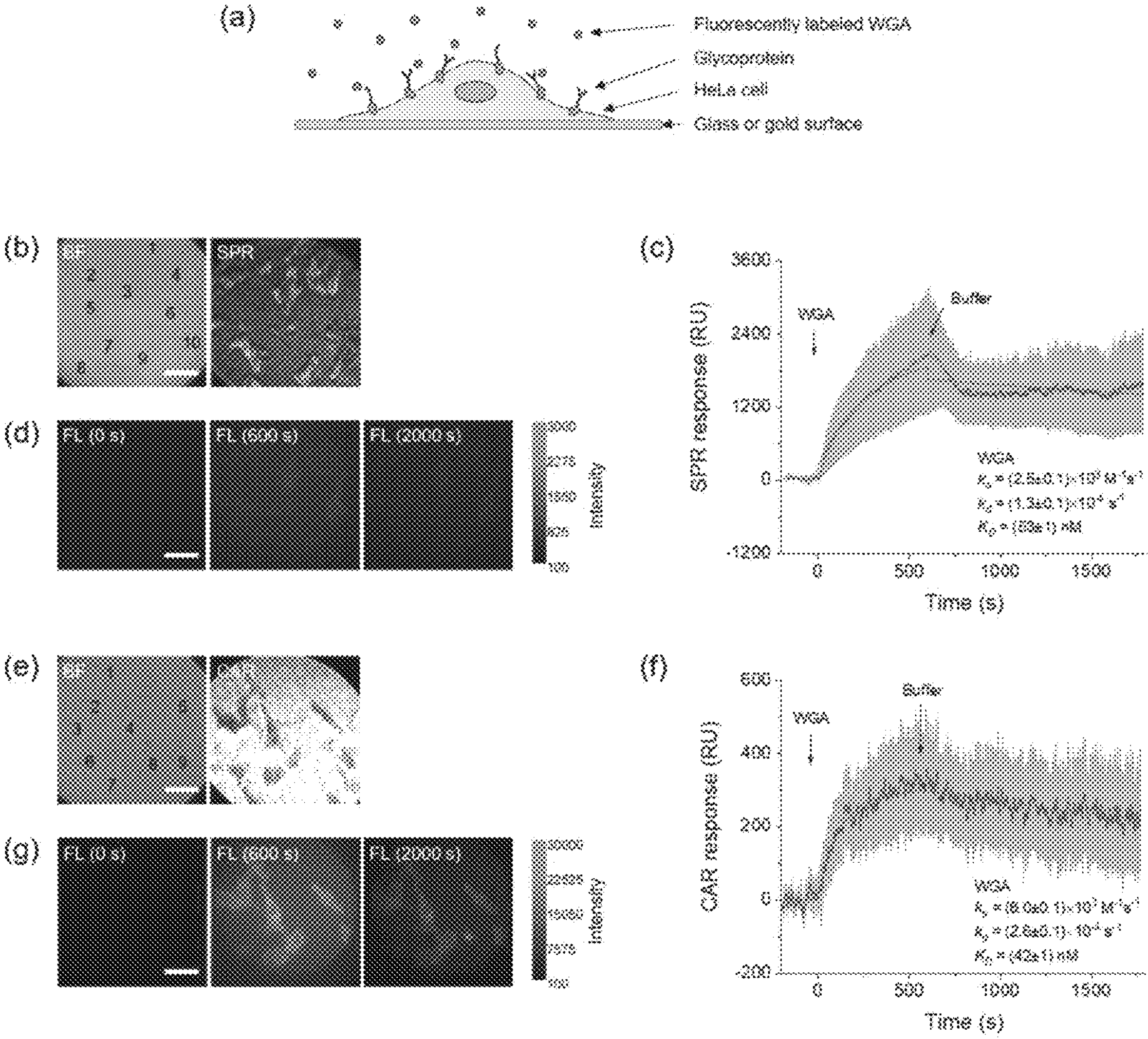
FIG. 7. Measuring WGA binding to glycoproteins on fixed HeLa cells. (a) HeLa cells were grown on a glass or gold surface for CAR or SPR measurements. The cells were fixed with 4% paraldehyde prior to measurements. Alexa Fluor 488-labeled WGA was flowed over the cells and allowed to bind to the glycoproteins on the cell membrane. (b) Bright field (BF) and SPR images of 10 cells on gold surface. (c) Glycoprotein-WGA binding kinetics measured by SPR. WGA concentration was 50 μg/ml. The black curve and gray shadows are the average SPR signal and standard deviation of the 10 cells (see FIG. 17*a* for details), respectively. The grey curve is fitting of the data to the first order kinetics. (d) Fluorescence (FL) images of the cells captured before WGA binding (0 s), after WGA binding (600 s) and after WGA dissociation (2000 s). Exposure time, 0.1 s. (e) BF and CAR images of 9 cells on glass surface. (f) Glycoprotein-WGA binding kinetics measured by CAR. WGA concentration was 50 μg/ml. The black curve and gray shadows are the average CAR signal and standard deviation of 8 out of the 9 cells (see FIG. 17*b* for details), respectively. The grey curve is fitting of the data to the first order kinetics. (g) Fluorescence images of the cells captured before WGA binding (0 s), after WGA binding (600 s) and after WGA dissociation (2000 s). Exposure time, 0.1 s. All the scale bars represent 5 m.

SPR was first used to measure glycoprotein-WGA interaction on fixed HeLa cells (FIG. 7*a*). The cells were cultured on a gold surface and fixed right before the measurement (FIG. 7*b*). PBS buffer was flowed over the surface to establish a baseline and then introduced 50 μg/ml WGA (FIG. 7*c*). Binding of WGA to the glycoproteins increased the surface refractive index and caused the SPR signal to increase. After the association process, PBS buffer was flowed in again to induce dissociation of WGA from the cells. The average SPR response of 10 cells was fitted to the first order kinetics, and $k_a$, $k_d$, and $K_D$ were determined to be $(2.5\pm0.1)\times10^3\ M^{-1}s^{-1}$, $(1.3\pm0.1)\times10^{-4}\ s^{-1}$, and 53±1 nM, respectively. The WGA was labeled with Alexa Fluor 488, allowing verification of the binding using fluorescence. Three fluorescence images were captured at different phases of the binding process: at the baseline, after association, and after dissociation (FIG. 7*d*) respectively. The fluorescence change, although weak, confirmed that the SPR signal was due to the binding.

Next, CAR imaging was used to repeat the glycoprotein-WGA binding measurement. The cells were cultured on a glass surface, and the bright field image and the corresponding CAR image of 9 cells are shown in FIG. 7*e*. The cells show dark patterns because they have higher refractive index than the background. $\theta_i$ was set at ~61.0 degrees with similar sensitivity to SPR. Kinetic constants for WGA were determined from the average CAR response of the 9 cells, with $k_a=(6.0\pm0.1)\times10^3\ M^{-1}s^{-1}$, $k_d=(2.6\pm0.1)\times10^{-4}\ s^{-1}$, and $K_D$=42±1 nM, respectively (FIG. 7*f*). The minor disagreement in kinetic constants might reflect different surfaces and different light illumination depth between SPR and CAR. Fluorescence images captured during the CAR measurement confirmed the binding of WGA (FIG. 7*g*). Notably, the fluorescence intensity on glass is over 30 times stronger than that on the gold surface, which is expected because gold is known to quench the fluorescence. For this reason, CAR is believed to be more compatible with fluorescence than SPR, and suitable for measuring biological samples that need simultaneous fluorescent labelling.

CAR Imaging of Ion Channel-Small Molecule Interaction on Cells

Figures 8A, 8B, 8C, 8D:
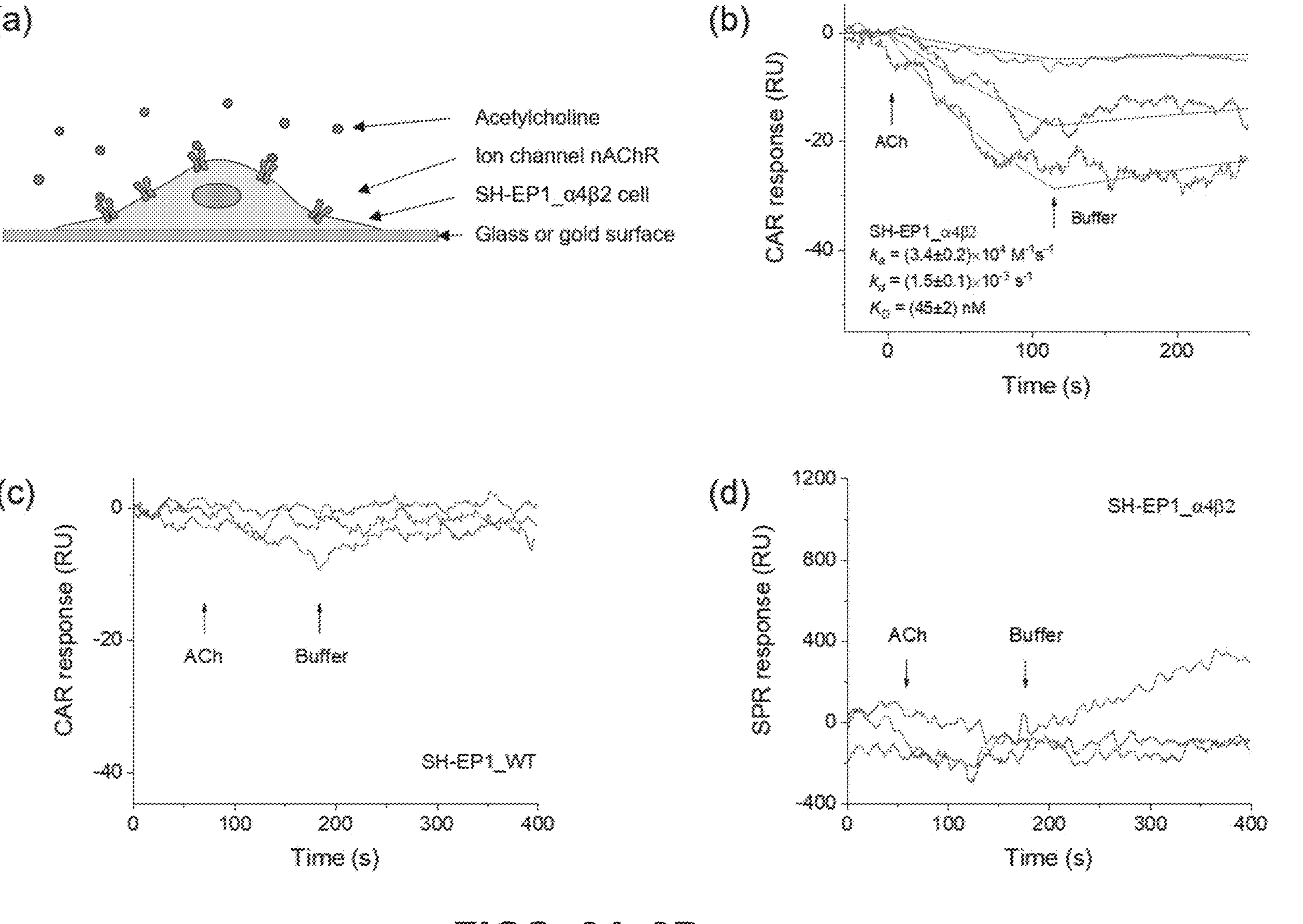
FIG. 8. Measuring acetylcholine binding to nAChR on SH-EP1_α4β2 cells. (a) SH-EP1_α4β2 cells were grown on a glass or gold surface for CAR or SPR measurements. The cells were fixed with 4% paraldehyde before the measurement. (b) Acetylcholine (ACh) binding to SH-EP1_α4β2 cells measured by CAR. CAR angle was parked at 61.6 degrees with a sensitivity of 112. The binding kinetic curves (black) were obtained by averaging the CAR response of 7 cells and globally fitted to the first order kinetics (grey) (see FIG. 18*b* for the response of individual cells). Acetylcholine concentrations: 25 nM, 100 nM and 200 nM. (c) Control experiments using wild type SH-EP1 cells which have no nAChR. Acetylcholine and PBS buffer were flowed to the cells as indicated by the arrows. No clear CAR response was observed (see FIG. 18*d* for individual cells). Acetylcholine concentrations: 50 nM, 100 nM and 200 nM. (d) Measuring acetylcholine binding to SH-EP1_α4β2 cells using SPR. No response was observed due to insufficient sensitivity of SPR (see FIG. 18*f* for individual cells). Acetylcholine concentrations: 50 nM, 100 nM and 200 nM.

Most drugs are small molecules, and over 50% drug targets are membrane proteins. SPR imaging can measure interactions directly on cells, but the sensitivity is inadequate for small molecule ligands. This weakness can be compensated by CAR owing to its tunable sensitivity. To demonstrate this capability, the binding kinetics between acetylcholine (182 Da), a small molecule neurotransmitter, and nicotinic acetylcholine receptor (nAChR), an ion channel membrane protein which is responsible for neurotransmission and drug addiction, were measured. nAChR was expressed on brain neuroblastoma SH-EP1 cells by transfecting the cells with human α4β2 receptor (SH-EP1_α4β2). In this experiment, $\theta_i$ was set at a high-sensitivity region (61.6 degrees), and acetylcholine solution was flowed over the cells (FIG. 8*a*). The averaged CAR responses of several cells were fitted globally as shown in FIG. 8*b*. The binding of acetylcholine induced negative change to the refractive index on the cell membrane. Although the binding of acetylcholine added mass to the surface, the binding also triggered cell membrane deformation and associated mass movement, which may reduce the effective refractive index on the sensor surface. To verify that the CAR signal was indeed due to acetylcholine binding, a control experiment was performed using wild type SH-EP1 cells which does not have nAChR. The CAR response was negligible (FIG. 8*c*). The acetylcholine-nAChR interaction was also measured using SH-EP1_α4β2 cells with SPR, which showed no measurable response due to insufficient sensitivity (FIG. 8*d*).

Sample Illumination Depth

Figures 9A, 9B, 9C:
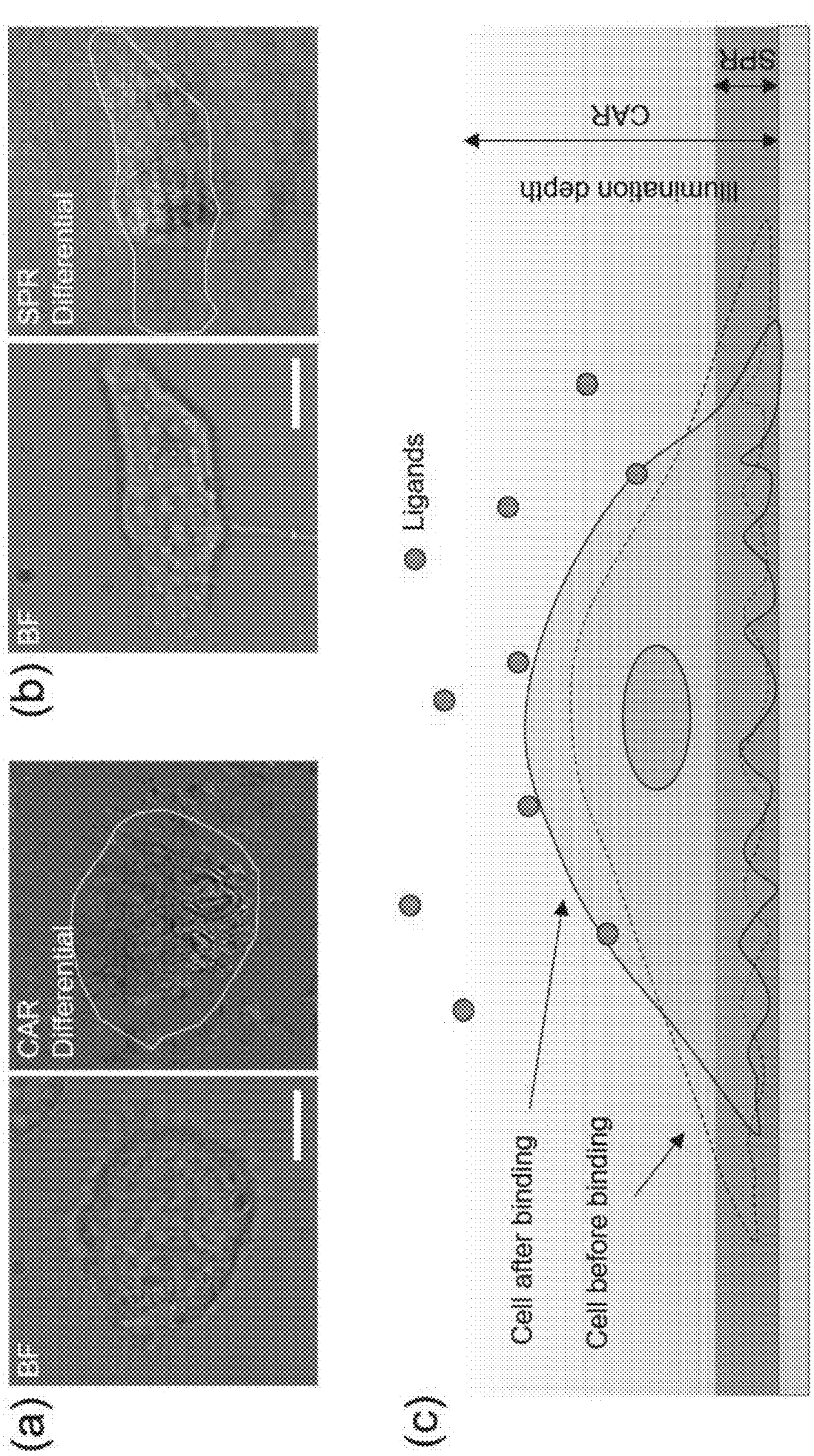
FIG. 9. Illumination depth of CAR and SPR. (a) Bright field (left) and differential CAR (right) images of a single cell. The differential CAR image was obtained by subtracting two consecutive frames in an image sequence recorded at 10 frames per second. The white line marks the outline of the cell. The parabolic patterns within the cell (marked by the grey square) are generated by the motion of organelles. (b) Bright field (left) and differential SPR images of a single cell. The images were captured and processed under the same condition as in (a). Organelle motion was not revealed by SPR. (c) Schematic picture showing illuminating a cell with CAR and SPR. SPR illuminates the sample with the surface-confined evanescent field and only the bottom section of the sample (several hundred nanometers) can be imaged. CAR has a portion of transmitted light additional to the deeper evanescent field, which enables CAR to see the binding-induced deformation of whole cell.

CAR has deeper illumination depth than SPR, which can be explained at least in part by the imaging principles of SPR and CAR. SPR occurs above critical angle, and the evanescent field is coupled by the excited surface plasmon, which concentrates the field in the vicinity of the surface (100-200 nm). In CAR, the incident light is below the critical angle, allowing a portion of light to go through the glass chip and illuminate the sample at further distances. Also, the evanescent field of CAR is less confined to the surface in the absence of surface plasmon. As an example, moving parabolic patterns were observed inside live cells under CAR illumination, which are organelles such as mitochondria (FIG. 9*a*). The parabolic shape arises from the interference between the evanescent wave and scattered light from the organelles. However, such patterns did not appear under SPR illumination (FIG. 9*b*), at least in part because the organelles are beyond the detection range of SPR.

The deeper illumination also reveals cell deformation caused by ligand binding (FIG. 9*c*). The CAR signal in WGA binding (FIG. 7*f*) and acetylcholine binding (FIG. 8*b*) reflects surface refractive index change caused by a combined effect of bound ligands induced surface mass increase and dynamic mass redistribution due to binding induced cell deformation. In both cases, ligand binding increases the surface refractive index because the refractive indices of the ligand molecules are higher than the buffer solution, and cell deformation decreases the surface refractive index because the mass center of the cell moves away from the surface. The mass of WGA induces more refractive index change than cell deformation, thus the net signal is positive. Acetylcholine is a small molecule, and the signal is dominated by cell deformation, so the net CAR signal is negative.

Figures 13A, 13B:
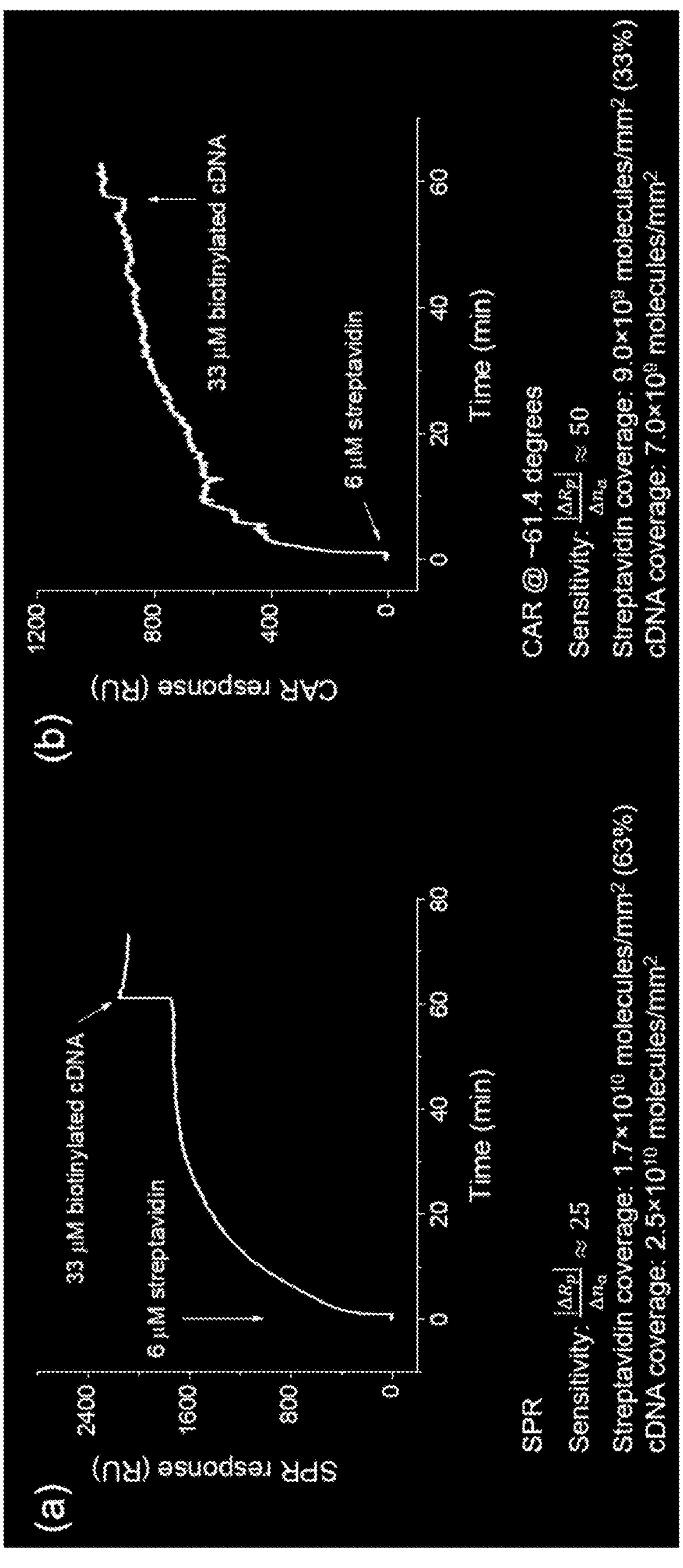
FIG. 13. Surface coverage of streptavidin and cDNA measured with SPR and CAR. (a) An NHS/EDC activated gold surface was placed on the SPR setup. 6 μM streptavidin was flowed to the surface to induce immobilization of the streptavidin. Then 33 μM biotinylated cDNA was introduced which bound to the surface via biotin-streptavidin conjugation. (b) Immobilization of streptavidin on an epoxy activated glass surface followed by cDNA conjugation. The concentrations of streptavidin and cDNA are the same as (a). CAR angle was parked at ~61.4 degrees with a medium-high sensitivity. Note that the fluctuations between 5-12 minutes are due to the floating impurities in solution.

For molecular interaction studies, the longer illumination depth of CAR could pick up background noises from impurities in the sample, because the motion of particles or aggregates in the sample solution will generate noise to the CAR signal (FIGS. 5*e* and 13*b*).

Wavelength of Incident Light

Another advantage of CAR over SPR is broader selection of light wavelength. SPR normally uses gold film and incident light with wavelength longer than 600 nm to generate SPR. In contrast, CAR is compatible with any wavelength in the visible range. In practice, shorter wavelengths (such as green/blue light) can be employed to achieve better spatial resolution and shorter penetration depth which reduces noise from the solution background. UV light also could be used to further improve the spatial resolution and sensitivity, as proteins and nucleic acids absorb lights in the UV range and the signal will be boosted. However, the optics and the camera also need to be UV compatible, and the UV light may cause damage to the sample.

Spatial Sensitivity Distribution

Figure 15A:
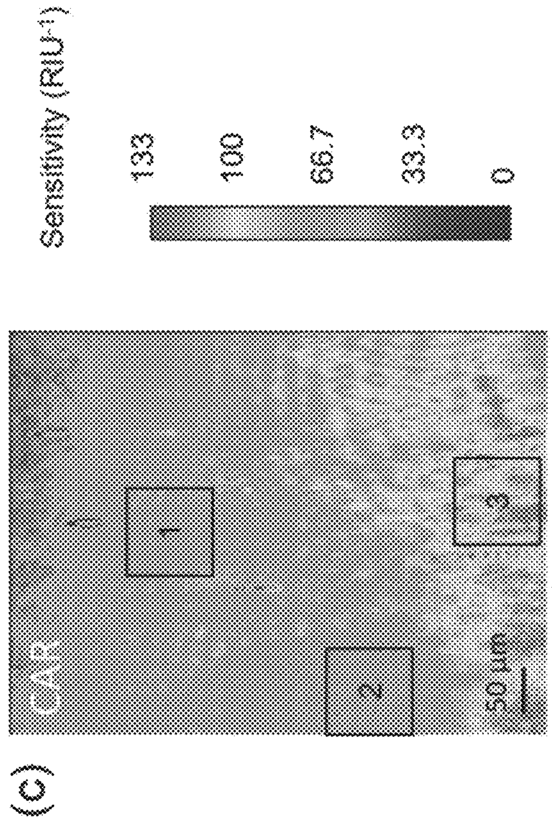
FIG. 15. Surface sensitivity distribution of CAR and SPR. (a) Spatial distribution of SPR sensitivity obtained by subtracting the images before and after 1% ethanol (final concentration) injection. (b) SPR response (reflectivity change) of the three regions of interests (ROIs) upon 1% ethanol injection. (c) CAR sensitivity is highly dependent on the incident angle. The angle was parked at ~61.5 degrees. The image shows the difference between before and after 1% ethanol injection, from which the sensitivity is calculated. The spatial distribution of sensitivity is non-uniform in vertical direction due to the slight difference in incident angle. (d) CAR response (reflectivity change) of the three ROIs upon 1% ethanol injection. The autosampler including the sample loop has a diffusion delay of less than 10 seconds.
Figure 15B:
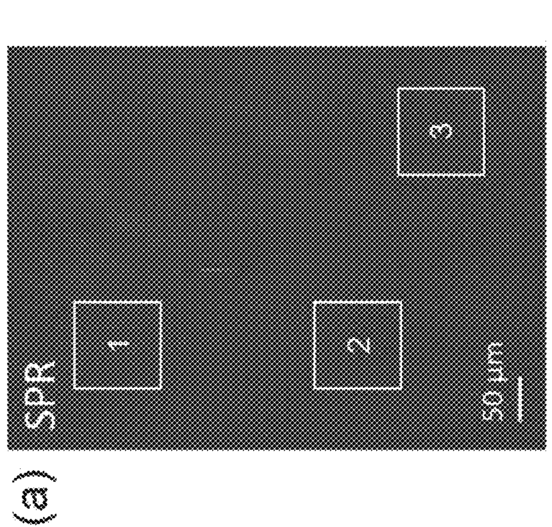
Figure 15C:
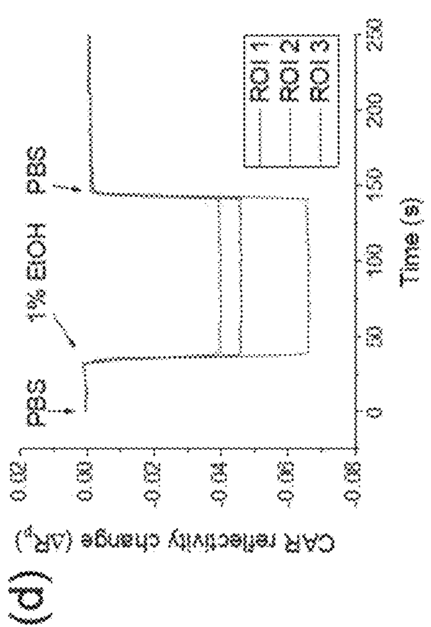
Figure 15D:
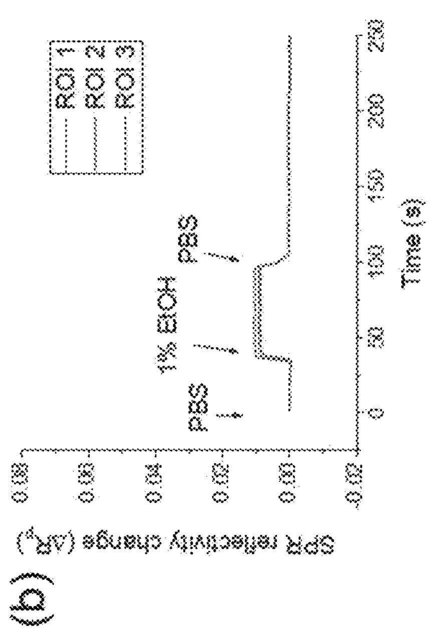
Figures 16A, 16B, 17A, 17B:
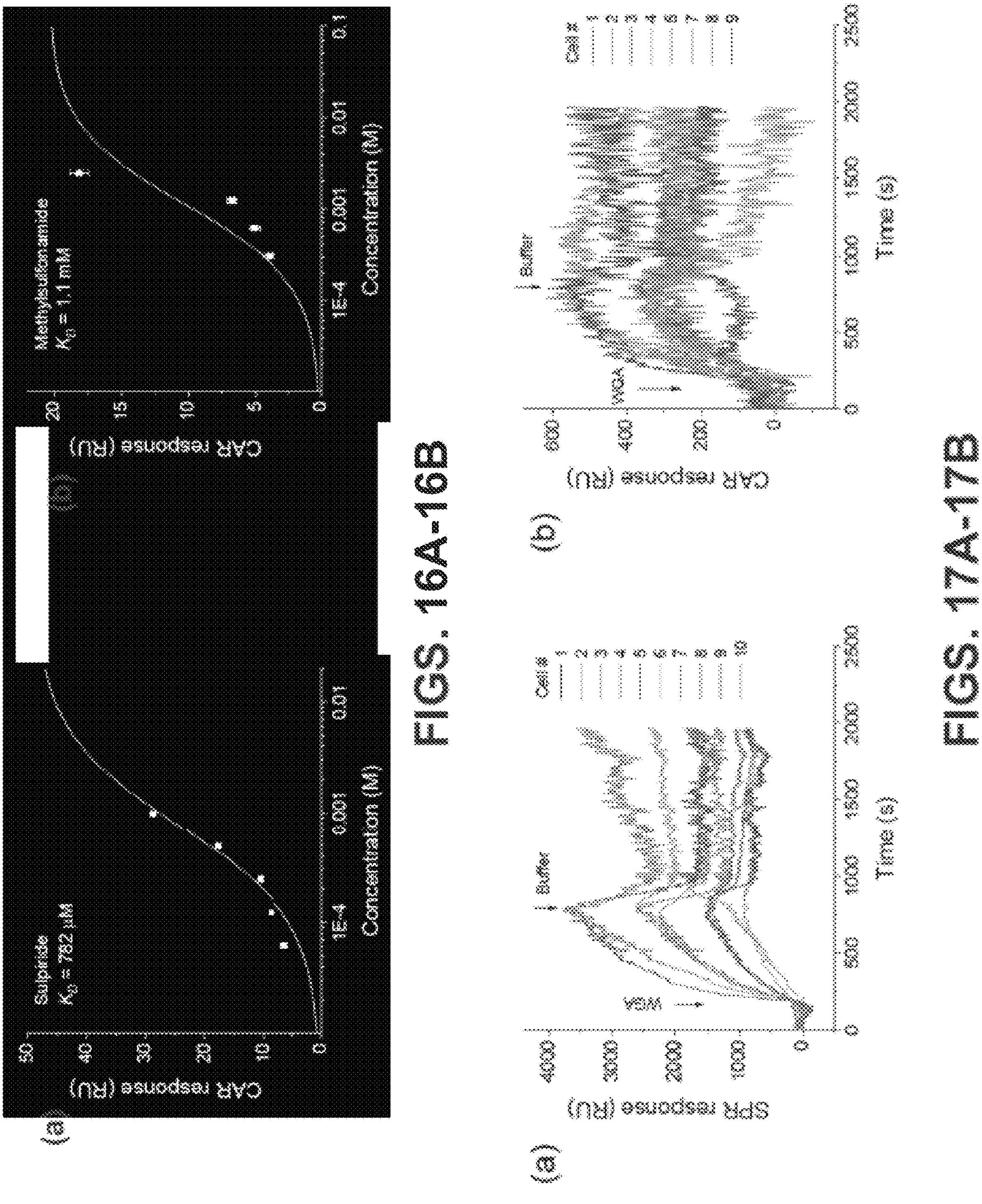
FIG. 16. Equilibrium analysis of sulpiride (a) and methylsulfonamide (b) binding to CAII. The dissociation constant ($K_D$) are 782 μM and 1.1 mM, respectively. The error bar represents standard deviation of the maximum response for each concentration in FIG. 3.
FIG. 17. WGA binding curves of individual fixed HeLa cells measured by SPR (a) and CAR (b).
Figures 18A, 18B, 18C, 18D, 18E, 18F:
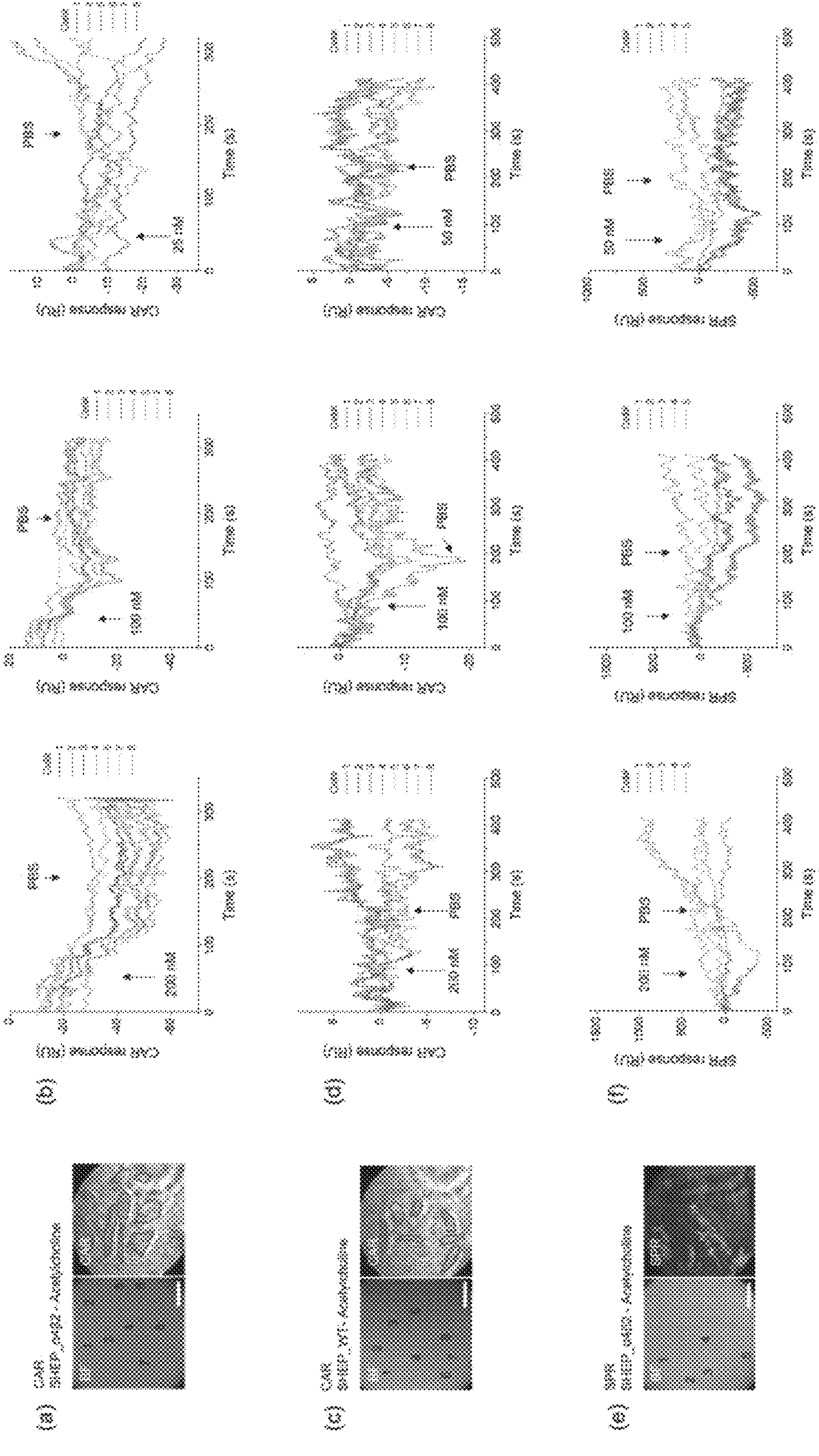
FIG. 18. Measuring acetylcholine-nAChR interaction with CAR and SPR. (a) Bright field (BF) and CAR images of 8 SH-EP1_α4β2 cells. The incident angle of CAR was parked at 61.6 degrees with high sensitivity of 112 $RIU^{-1}$. Because the angle was close to the critical angle, the cells (marked in grey) only had little difference from the glass background which already reached critical angle. (b) CAR response of the cells upon flowing 200 nM (left), 100 nM (middle) and 25 nM (right) acetylcholine. (c) Control experiments: BF and CAR images of 8 wild type SH-EP1 cells. (d) CAR response of the cells upon flowing 200 nM (left), 100 nM (middle) and 50 nM (right) acetylcholine. (e) Measuring acetylcholine binding with SPR. BF and SPR images of 5 SH-EP1_α4β2 cells. (f) SPR response of the cells upon flowing 200 nM (left), 100 nM (middle) and 50 nM (right) acetylcholine.

The incident light in SPR imaging setup may not illuminate the surface at perfectly uniform angle, which also varies with different instruments. The slight angle difference can barely affect the sensitivity of SPR because SPR has constant sensitivity near the SPR angle (FIG. 15*a*). For CAR, however, the sensitivity is dependent on the incident angle, and the imperfect illumination could lead to a non-uniform surface sensitivity (FIG. 15*c*). The CAR sensitivity of the prism-based setup, calibrated with 1% ethanol, was found to differ by up to 4 times by different regions. The microscope-based setup showed a more uniform sensitivity at least in part because of tunable collimation of incident light and smaller illumination area.

Detection Limit

Figure 19:
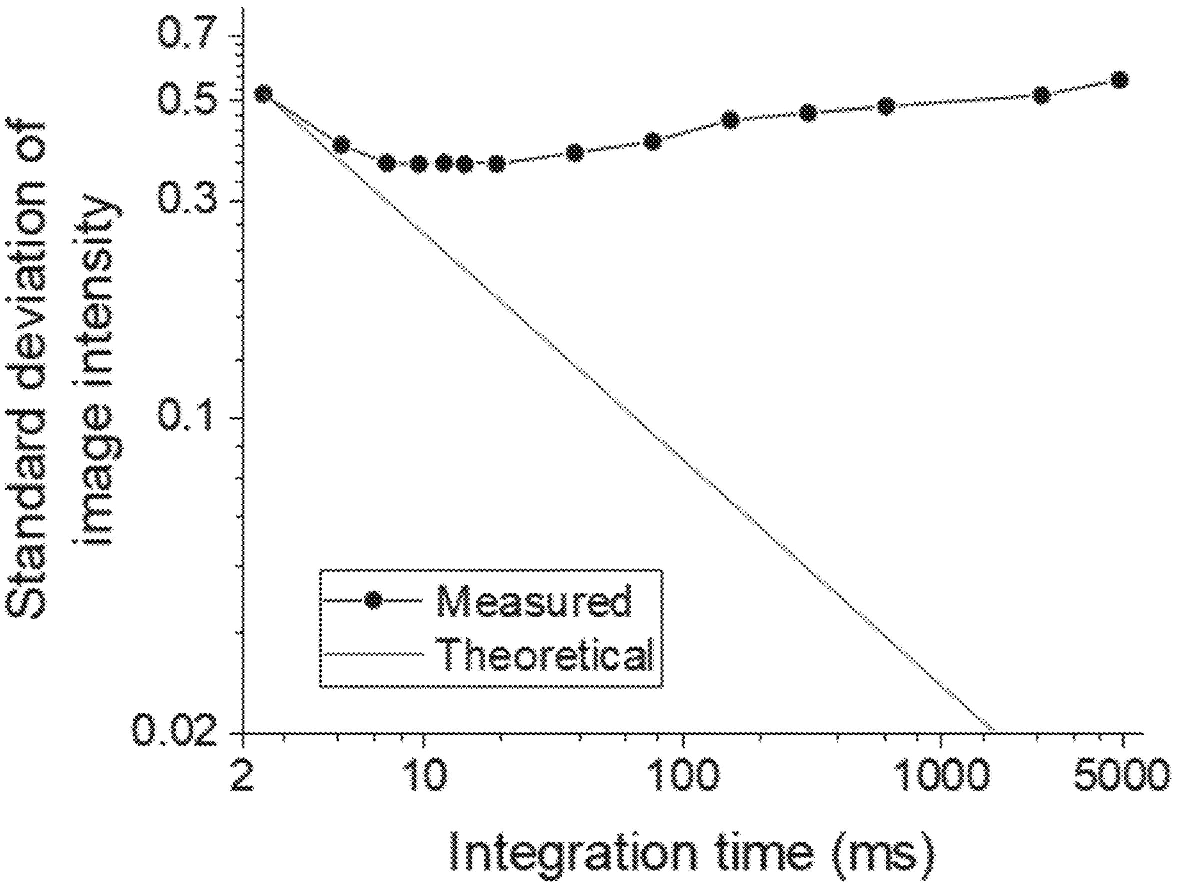
FIG. 19. System noise analysis. Total noise (black) and shot noise (grey) were calculated using a method by Piliarik et al., Direct optical sensing of single unlabeled proteins and super-resolution imaging of their binding sites. Nature Communications 5, 4495 (2014). An image sequence was recorded at 500 frames per second for 1 min. The images were averaged over different periods and the new image sequences were differentiated. Standard deviation of the differentiated image sequence was calculated and plotted vs. the integration time. At 1 s which is the typical sampling rate for biosensors, the total noise is 25 times larger than the shot noise.

Detection limit is determined at least in part by the noise level and sensitivity. For CAR at high angle, the noise level is $1.7\times10^{-4}$ (unit: reflectivity) (FIG. 12*d*) and the sensitivity is 112 (unit: reflectivity per refractive index unit ($RIU^{-1}$)) (FIG. 4*d*). The noise thus corresponds to $1.5\times10^{-6}$ RIU, or 1.5 RU, or 1.5 $\mu g/mm^2$ in mass density. Similarly, the noise for SPR is determined to be 2.4 $\mu g/mm^2$. The sensitivity is intrinsic property of CAR (at a specific angle) and SPR and could not be changed for a given instrument. Therefore, one way to lower the detection limit is to reduce noise. In one scenario, the smallest noise for optical sensors is the shot noise, which is due to the quantum nature of light. To reach shot noise limit, all other types of noise are typically well under control, such as light source noise and environmental and system mechanical noise. The theoretical shot noise for the prism-based setup was calculated to be 25 times lower than the measured noise (FIG. 19). The identified major noise source is mechanical noise from the system cooling fans. Therefore, over an order of magnitude lower detection limit could be reached if the system mechanical noise is reduced with a quiet cooling design.

Incident Light Polarization

CAR is not limited by light polarization, and thus does not require p-polarized light. Both p- and s-polarized light present similar sensitivity and dynamic range in CAR (FIGS. 10 and 20), indicating CAR measurements can be performed using either or both polarizations at the same time. This capability may allow CAR to measure polarization-sensitive samples and obtain polarization-dependent contrast to determine the anisotropy, orientations and orientational dynamics of the samples Cost Efficiency CAR uses regular microscope cover glass which typically costs about $0.15 each (22×22 mm, No. 1 cover glass, VWR). In SPR, the gold coated cover glass (without surface functionalization) is ~$30 per chip (Biosensing Instrument) which is 200 times more expensive. The surface functionalization of glass chip uses standard silane surface chemistry, comparable to the gold surface chemistry in terms of reagent cost and workload.

Experimental Setup

The SPR and CAR measurements for principle demonstration (FIG. 4) and protein, miRNA, and small molecule detections (FIGS. 5-6) were conducted using a commercial prism-based SPR imaging system (SPRm 200, Biosensing Instrument Inc., Tempe, Arizona) with a 690 nm, 1 mW laser, and a custom installed USB3 CMOS camera (MQ003MG-CM, XIMEA, Germany). The system has 20× magnification. Samples were delivered to the system via an autosampler (BI autosampler, Biosensing Instrument Inc.).

All the cell-related experiments including CAR, SPR, transmitted and fluorescence measurements (FIGS. 7-9) were performed on an objective-based SPR microscope setup, which consisted of an inverted microscope (Olympus IX-81) and a 60× (NA 1.49) oil-immersion objective. The light source for CAR and SPR imaging was a superluminescent light emitting diode (SLD-260-HP-TOW-PD-670, Superlum, Ireland) with 670 nm wavelength. The light source for transmitted and fluorescence imaging were the stocking halogen and mercury lamp of the microscope, respectively. A CMOS camera (ORCA-Flash 4.0, Hamamatsu) was used to record the images. A gravity-based drug perfusion system (SF-77B, Warner Instruments, Connecticut) was used for delivering analytes to the cells.

Materials

Cover glass (No. 1) for CAR measurements were purchased from VWR. The cover glass was coated with 1.5 nm Cr followed by 43 nm gold using an e-beam evaporator for SPR measurements. (3-glycidyloxypropyl)trimethoxysilane, N-hydroxysulfosuccinimide sodium salt (NHS), N-(3-dimethylaminopropyl)-N'-ethylcarbodiimide hydrochloride (EDC), O-(2-Carboxyethyl)-O'-(2-mercaptoethyl)heptaethylene glycol (SH-PEG8-COOH), bovine serum albumin (BSA), carbonic anhydrase lysozyme II from bovine erythrocytes (CAII), furosemide, sulpiride, methylsulfonamide, and acetylcholine perchlorate were purchased from Sigma-Aldrich. Mouse anti-cattle bovine serum albumin monoclonal antibody (anti-BSA) was purchased from MyBioSource. MicroRNA-21 (5'-UAG CUU AUC AGA CUG AUG UUG A-3' (SEQ ID NO: 1)) and biotinylated complementary DNA (5' biotin-AAAAA TCA ACA TCA GTC TGA TAA GCT A-3' (SEQ ID NO: 2)) were purchased from Integrated DNA Technologies. Streptavidin, methyl-PEG4-thiol (MT (PEG)4), and wheat germ agglutinin (WGA) with Alexa Fluor 488 tag were purchased from Thermo Fisher Scientific. Phosphate buffered saline (PBS) was purchased from Corning. Deionized water with resistivity of 18.2 MΩ/cm was used in all experiments.

Surface Functionalization

The gold surface was rinsed with ethanol and water each for three times and then annealed with hydrogen flame. The cleaned chips were incubated in 0.2 mM SH-PEG8-COOH and 0.2 mM MT(PEG)4 in PBS overnight. Then the —COOH groups were activated by incubating in a mixture of 50 mM NHS and 200 mM EDC for 20 minutes. 5 μM BSA, 2.2 μM CAII, or 6 μM streptavidin was applied to the surface immediately and incubated for one hour. The remaining activated sites were quenched with 20 mM ethanolamine for 10 minutes. Finally, the CAII and streptavidin functionalized surfaces were incubated with 1 mg/ml BSA solution to block non-specific binding sites. To immobilize cDNA on the surface, 33 μM biotinylated cDNA was applied to the streptavidin functionalized surface and incubated for one hour.

The glass chip was rinsed with ethanol and water for three times. Then the chips were dried with $N_2$, treated with oxygen plasma, and incubated in 1% (3-glycidyloxypropyl) trimethoxylsilane in isopropanol overnight. After rinsed with isopropanol and DI water, the chips were immediately incubated with 5 μM BSA, 2.2 μM CAII, or 6 μM streptavidin for one hour. Next, 20 mM ethanolamine was used to quench the unreacted sites for 5 minutes, and 1 mg/ml BSA was applied to the CAII and streptavidin coated chips for 10 minutes to block non-specific sites. cDNA was immobilized on the streptavidin coated surface by incubation in 33 μM biotinylated cDNA solution for one hour.

Cell Culture

HeLa, SH-EP1, and SH-EP1_α4β2 cells were obtained from the American Type Culture Collection. The cells were cultured in Dulbecco's modified eagle medium (Lonza) with 10% fetal bovine serum (Invitrogen) and 1% penicillin and streptomycin in a humidified incubator at 37° C. with 5% $CO_2$. The cells were harvested at 75% confluence, transferred to glass or gold coated glass chips, and cultured overnight before experiments. The glass and gold surfaces were pretreated with 0.3 mg/ml collagen type IV (Sigma-Aldrich) to improve cell attachment to the surface. For experiments using fixed cells, the cells were fixed with 4% paraformaldehyde solution (Santa Cruz Biotechnology) for 20 minutes, washed with PBS and immediately placed on instrument for measurement.

Inc.) and Fiji. Response curve fitting and binding kinetics constant calculation were carried out with ImageAnalysis and Scrubber (BioLogic Software).

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

```
SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

uagcuuauca gacugauguu ga                                              22


<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

aaaaatcaac atcagtctga taagcta                                         27
```

Simulation and Data Processing

WinSpall 3.01 (Resonant Technologies GmbH, Germany) was used to calculate the reflectivity as a function of incident angle for CAR and SPR. The recorded CAR and SPR images were processed with ImageAnalysis (Biosensing Instrument

What is claimed is:

1. A method of detecting molecular interactions, the method comprising:

contacting a liquid comprising a ligand with a first surface of a substrate functionalized with a receptor displayed on a surface of a cell that is disposed on the first surface of the substrate, wherein the substrate is optically transparent bare glass free of a coating and wherein a refractive index of the substrate exceeds a refractive index of the liquid;

introducing an incident light into an optical prism toward a second surface of the substrate at an incident angle with respect to a plane perpendicular to the first surface of the substrate, wherein the second surface is opposite the first surface and the incident angle is less than a critical angle defined as $\sin^{-1}(n_a/n_g)$, wherein $n_g$ is the refractive index of the substrate and $n_a$ is the refractive index of the liquid;

obtaining one or more differential critical angle reflection (CAR) images of the cell from light reflected at an interface of the liquid and the first surface of the substrate; and identifying one or more moving parabolic patterns within the cell in the differential CAR images and/or a cell membrane deformation of the cell and a surface refractive index change in the differential CAR images, thereby detecting the molecular interactions.

2. The method of claim 1, wherein the moving parabolic patterns are generated by motion of one or more organelles within the cell.

3. The method of claim 1, wherein the ligand, the receptor, or both comprise a molecule.

4. The method of claim 3, wherein the molecule comprises a nucleic acid or a protein.

5. The method of claim 1, further comprising tuning a sensitivity and dynamic range to selected levels by varying the incident angle.

6. The method of claim 1, wherein a sensitivity of the method increases as the incident angle approaches the critical angle.

7. The method of claim 1, further comprising monitoring interaction of the ligand and the receptor in real time.

8. The method of claim 1, wherein binding of the ligand by the receptor alters an effective refractive index of the substrate near the first surface of the substrate.

9. The method of claim 1, further comprising fluorescence imaging of the ligand, the receptor, or both.

10. The method of claim 1, wherein the incident light comprises p-polarized light, s-polarized light, non-polarized light, or circularly polarized light.

11. An optical imaging system comprising:

an optically transparent substrate having a first surface and a second surface opposite the first surface, wherein the optically transparent substrate is bare glass free of a coating and wherein the first surface of the optically transparent substrate is functionalized with a receptor displayed on a surface of a cell that is disposed on the first surface of the optically transparent substrate;

an optical prism configured to be coupled to the second surface of the optically transparent substrate;

a light source configured to introduce collimated light into the optical prism at an incident angle with respect to a plane perpendicular to the second surface of the optically transparent substrate, wherein the incident angle is less than a critical angle defined as $\sin^{-1}(n_a/n_g)$, wherein $n_g$ is a refractive index of the substrate and $n_a$ is a refractive index of the liquid, and wherein the light source is further configured to vary the incident angle to tune a sensitivity and dynamic ranges to selected levels;

a detector configured to obtain one or more differential critical angle reflection (CAR) images of the cell from light reflected from an interface of the first surface of the optically transparent substrate and a liquid in contact with the first surface of the optically transparent substrate; and a processor configured to identify one or more moving parabolic patterns within the cell in the differential CAR images and/or a cell membrane deformation of the cell and a surface refractive index change in the differential CAR images when a liquid comprising a ligand is contacted with the first surface of the optically transparent substrate.

12. The optical imaging system of claim 11, wherein the moving parabolic patterns are generated by motion of one or more organelles within the cell.

13. The optical imaging system of claim 11, wherein the ligand, the receptor, or both comprise a molecule.

14. The optical imaging system of claim 13, wherein the molecule comprises a nucleic acid or a protein.

15. The optical imaging system of claim 11, wherein the collimated light comprises visible light or UV light; or, wherein the collimated light comprises p-polarized light, s-polarized light, non-polarized light, or circularly polarized light.

* * * * *